United States Patent
Pitt et al.

(10) Patent No.: US 10,457,975 B1
(45) Date of Patent: Oct. 29, 2019

(54) HOLLOW ROTATING DEVICE FOR SEPARATING PARTICLES FROM BLOOD

(71) Applicants: William George Pitt, Orem, UT (US); Daniel S. McClellan, Provo, UT (US); Colin G. Bledsoe, Springville, UT (US); Mahsa Alizadeh, Provo, UT (US)

(72) Inventors: William George Pitt, Orem, UT (US); Daniel S. McClellan, Provo, UT (US); Colin G. Bledsoe, Springville, UT (US); Mahsa Alizadeh, Provo, UT (US)

( * ) Notice: Subject to any disclaimer, the term of this patent is extended or adjusted under 35 U.S.C. 154(b) by 117 days.

(21) Appl. No.: 15/429,106

(22) Filed: Feb. 9, 2017

Related U.S. Application Data

(60) Provisional application No. 62/293,630, filed on Feb. 10, 2016.

(51) Int. Cl.
*C12Q 1/24* (2006.01)
*C12Q 1/04* (2006.01)
*C12Q 1/10* (2006.01)

(52) U.S. Cl.
CPC .............. *C12Q 1/24* (2013.01); *C12Q 1/04* (2013.01); *C12Q 1/10* (2013.01)

(58) Field of Classification Search
CPC .............. C12Q 1/24; C12Q 1/04; C12Q 1/10
See application file for complete search history.

(56) References Cited

U.S. PATENT DOCUMENTS

| | | | | |
|---|---|---|---|---|
| 2007/0087429 A1* | 4/2007 | Tanimoto | ............. | G01N 35/025 435/287.2 |
| 2009/0291818 A1* | 11/2009 | Soares | ................... | B01D 43/00 494/34 |
| 2014/0045672 A1* | 2/2014 | Galavotti | ............. | B04B 5/0442 494/44 |

OTHER PUBLICATIONS

Antranik.org, Blood Components, Hemoglobin, Type/Rh Factor, Agglutination, Dec. 4, 2011, as shown as available on Apr. 23, 2012 by Internet Archive Wayback Machine, Available online at: web.archive.org/web/20120423223017/https://antranik.org/blood-components-hemoglobin-typerh-factor-agglutination.*

Dhurat et al., Principles and Methods of Preparation of Platelet-Rich Plasma: A Review and Author's Perspective, J Cutan Aesthet Surg., Oct.-Dec. 2014; 7(4): 189-197.*

Hiemenz and Rajagopalan, Principles of Colliod and Surface Chemistry, p. 68-85, 1997.

Cooney, David O., Biomedical Engineering Principles, p. 42-57, 1976.

Shu Chien and Richard Skalak, Handbook of Bioengineering, p. 14.10-14.15, 1987.

Patel, Outcomes of Carbepenem-Resistant Klebsiella Pneumoniae Infection and the Impact of Antimicrobial and Adjunctive Therapies, Infection Control and Hospital Epidemiology, Dec. 2008, vol. 29, No. 12.

Olaf Neth, Dominic L. Jack, Alister W. Dodds, Helen Holzel, Nigel J. Klein, and Malcolm WL. Turner, Mannose-Binding Lectin Binds to a Range of Clinically Relevant Microorganisms and Promotes Complement Deposition, Infection and Immunity, Feb. 2000, p. 688-693.

Anand Kumar, Dainel Roberts, Kenneth Wood, Bruce Light, Joseph Parrillo, Satendra Sharma, Robert Suppes, Dainel Feinstein, Sergio Zanotti, Leo Taiberg, David Gurka, Aseem Kumar, Mary Cheang, Duration of hypotension before initiation of effective antimicrobial therapy is the critical determinant of survival in human septic shock, Critical Care Medicine, p. 1589-1596, 2006.

Sharon Kleinschmidt, Flavia Hugygens, Joan Faoagali, Irani U Rathnayake, and Louise M Hafner, *Staphylococcus epidermidis* as a cause of bacteremia, Future Microbiology, 2015 10(11).

Johannes Hedman and Peter Radstrom, Overcoming inhibition in real-time, Methods in Molecular Biology, vol. 943, p. 17-48, 2013.

Meng Gao, Qinglian Hu, Guangxue Feng, Nikodem Tomczak, Rongrong Liu, Bengang Xing, Ben Zhong Tang, and Bin Liu, A multifunctional probe with aggregation-induced emission characteristics for selective fluorescence imaging and photodynamic killing of bacteria over mammalian cells, Advanced Healthcare Materials, 2015, 4, p. 659-663.

Daniel J. Diekema and Michael A. Pfaller, Rapid detection of antibiotic-resistant organism carriage for infection prevention, Clinical Infectious Diseases, 2013, p. 1614-1620.

Yu W. Chu, David A. Engebretson, and James R. Carey, Bioconjugated magnetic nanoparticles for the detection of bacteria, Journal of biomedical nanotechnology, vol. 9, p. 1951-1961, 2013.

Jacob S. Beveridge, Jason R. Stephens, and Mary Elizabeth Williams, The use of magnetic nanoparticles in analytical chemistry, Annual Review of Analytical Chemistry, 2011, p. 251-273.

A.P. Hooper and W.G.C. Boyd, Shear-flow instability at the interface between two viscous fluids, Journal of fluid mechanics, 1983, vol. 128, pp. 507-528.

Pablo Yagupsky and Frederick S. Nolte, Quantitative aspects of septicemia, Clinical microbiology reviews, Jul. 1990, p. 269-279.

Shuqi Wang, Fatih Inci, Tafadzwa L. Chaunzwa, Ajay Ramanujam, Aishwarya Vasudevan, Sathya Subramanian, Alexander Chi Fai IP, Banupriya Sridharan, Umut Atakan Gurkan, Utkan Demirci, Portable microfluidic chip for detection of *Escerichia coli* in produce and blood, International journal of nanomedicine, p. 2591-2600, 2012.

(Continued)

*Primary Examiner* — Jennifer M. H. Tichy
(74) *Attorney, Agent, or Firm* — James Sonntag

(57) ABSTRACT

Provided herein is a method and a system for separating suspended particles that have differing sedimentation velocities, comprising placing the particles inside a hollow device which upon rotation, spins the suspension into a thick film within which sedimentation of the particles occurs, rotating the hollow device at a speed and for a time that allows fast-sedimenting particles to sediment into a layer of more densely packed particles while some of the slow-sedimenting particles remain outside of the dense-particle-pack, and slowing the rotation of the hollow device in a manner to prevent remixing of the layer of dense-particle-pack with a layer containing some of the slow-sedimenting particles. This method may have application in many technologies including the rapid separation of bacteria from blood components.

13 Claims, 10 Drawing Sheets

(56) References Cited

OTHER PUBLICATIONS

Dino Di Carlo, Inertial microfluidics, The royal society of chemistry, 2009, p. 3038-3046.

W. Matthew Leevy, James R. Johnson, C. Lakshmi, Joshua Morris, Manuel Marquez, and Bradley D. Smith, Selective recognition of bacterial membranes by zinc(II)-coordination complexes, Chemical communications—The Royal society of chemistry, 2006, p. 1595-1597.

Zhigang Wu, Ben Willing, Joakim Bjerketorp, Janet K. Jansson, and Klas Hjort, Soft inertial microfluidics for high throughput separation of bacteria from human blood cells, the royal society of chemistry, 2009, p. 1193-1199.

Pratik Pranay, Rafael G. Henriquez-Rivera, and Michael D. Graham, Depletion layer formation in suspensions of elastic capsules in newtonian and viscoelastic fluids, Physics of fluids, 24, 2012.

Albert J. Mach, Dino Di Carlo, Continuous scalable blood filtration device using inertial microfluidics, Biotech and bioengineering, vol. 107, No. 2, Oct. 1, 2010, p. 302-311.

Mary Amasia and Marc Madou, Large-volum centrifugal microfluidic device for blood plasma separation, future Science—Bioanalysis, p. 1701-1710, 2010.

Jung-Jae Lee, Kyung Jae Jeong, Michinao Hashimoto, Albert H. Kwon, Alina Rwei, Sahadev A. Shankarappa, Jonathan H. Tsui, and Daniel S.Kohane, Synthetic ligand-cotaed magentic nano-particles for microfluidic bacterial separation from blood, Nano Letters, 2014, p. 1-5.

Inger Mattsby-Baltzer, Tomas Bergstrom, Keith McCrea, Robert Ward, Lars Adolfsson, and Olle Larm, Affinity apheresis for treatment of bacteremia caused by *Staphylococcus aureus* and/or methicillin-resistant *S. aureus* (mrsa), Journal of microbiology and biotechnology, 2011, p. 659-664.

Han Wei Hou, Hiong Yap Gan, Ali Asgar S. Bhagat, Leon D. Li, Chwee Teck Lim, and Jongyoon Han, A microfluidics apporach towards high-throughput pathogen removal from blood using margination, Biomicrofluidics, 2012, 024115.

Stefan Haeberle, Thilo Brenner, Roland Zengerle and Jens Ducree, Centrifugal extraction of plasma from whole blood on a rotating disk, Lab Chip—The Royal Society of Chemistry, 2006, p. 776-781.

Joo H. Kang, Michael Super, Chong Wing Yung, Ryan M. Cooper, Karel Domansky, Amanda R. Graveline, Tadanori Mammoto, Julia B. Berthet, Heather Tobin, Mark J. Cartwright, Alexander L. Watters, Martin Rottman, Anna Waterhouse, Akiko Mammoto, Nazita Gamini, Melissa J. Rodas, Anxhela Kole, Amanda Jiang, Thomas M. Valentin, Alexander Diax, Kazue Takahashi, and Donald E. Ingber, An extracorporeal blood-cleasning device for sepsis therapy, Nature, 2014.

* cited by examiner

HOLLOW ROTATING DEVICE FOR SEPARATING PARTICLES FROM BLOOD

CROSS-REFERENCE TO RELATED APPLICATIONS

This application claims priority to U.S. Provisional Patent Application No. 62/293,630 entitled "Hollow Rotating Device for Separating Plasma and Bacteria from Blood" and filed on 10 Feb. 2016 for William G. Pitt, which is incorporated herein by reference.

STATEMENT REGARDING FEDERALLY SPONSORED RESEARCH OR DEVELOPMENT

This invention was made with government support under grant R01AI116989 awarded by The National Institutes of Health. The government has certain rights in the invention.

BACKGROUND OF THE INVENTION

The technology provided herein relates to the rapid separation and collection of particles suspended in a fluid and more particularly relates to the rapid separation of bacteria from blood to be used for diagnosis of blood infections.

Suspended particles of similar density are very difficult to separate from each other by isopycnic centrifugation. If their sizes are slightly different, separation by filtering becomes challenging particularly if the smaller sized particle is also in the minority by number, as the high number of large particles will block the filter pores and prevent many of the small particles from passing. There are methods such as cross-flow filtration in which the large particles are swept laterally away from the pores so the small particles can pass; however this method is often time consuming and requires large volumes of fluid for the cross-flow filtration process. In cases with requirements of rapid separation with very little process fluid, sedimentation remains a convenient process that can separate particles of similar density and slightly different size, even when the small particles are in the vast minority. While sedimentation can be used to separate any set of particles that have differing sedimentation velocities, sedimentation is particularly useful to separate smaller bacteria in concentrations of hundreds per milliliter from slightly larger red blood cells in concentrations of billions per milliliter, in a rapid manner without requiring or producing large amounts of excess liquid.

BRIEF SUMMARY OF THE INVENTION

Reference throughout this specification to features or similar language does not imply that all of the features that may be realized with the present invention should be or are in any single embodiment of the invention and method of use. Rather, language referring to the features is understood to mean that a specific feature or characteristic described in connection with a method or an embodiment is included in at least one embodiment of the present invention. Thus, discussion of the methods, features and characteristics, and similar language, throughout this specification may, but do not necessarily, refer to the same embodiment.

Furthermore, the described features, characteristics and methods of the invention may be combined in any suitable manner in one or more embodiments. One skilled in the relevant art will recognize that the invention can be practiced without one or more of the specific features or characteristics of a particular embodiment. In other instances, additional features and characteristics may be recognized in certain embodiments that may not be present in all embodiments of the invention and its method of use.

The features and characteristics of the present invention will become more fully apparent from the following description and appended claims, or may be learned by the practice of the invention as set forth hereinafter.

Provided herein is a method for the batchwise separation of suspended particles which have differing sedimentation velocities, wherein the suspension of particles is placed inside a carefully constructed hollow device. When rotated, the blood is spun into a channel on the inside surface of the wall of the hollow device, forming a thick film of blood. Sedimentation of the fast-sedimenting particles moves the particles toward the outward edge of the fluid film where they are concentrated into a higher particle density than found in the original fluid. (In this specification, "inward" refers to a direction toward the axis of rotation and "outward" refers to a direction away from the axis of rotation.) The slow-sedimenting particles require longer time to sediment toward the outward edge of the thick film. When the spinning is stopped at a time after the fast-sedimenting particles have formed a layer of higher particle density, and a time before all of the slow-sedimenting particles have arrived at that layer, many of the slow-sedimenting particles remain in the layer that has been clarified of most of the fast-sedimenting particles. This clarified layer, that still contains some slow-sedimenting particles, can then be separated from the layer of fast-sedimenting particles.

Further provided herein is a method wherein the particles to be separated are of biological origin, such as red blood cells (RBCs), white blood cells (WBCs), platelets, or microorganisms.

Featured herein is a description of several embodiments of hollow devices, which when rotated, spread the particle suspension into thick layers between 0.2 and 10 millimeters (mm). Some of the elements of these unique hollow devices that lead to the sedimentation-driven separation of particles and their passive separation from each other after rotation has stopped are the vestibule for the fluid, a trough for retaining the fast-sedimenting particles, and a weir, over which the fluid containing the slow-sedimenting particles flows after the rotation stops.

Herein provided is a method of slowing the rotating hollow device at a varying or at a constant rate of deceleration that will prevent the remixing of the separated fluid layers containing the fast-sedimenting particles and the slow-sedimenting particles, a method which is crucial to the successful implementation of this technology.

Herein provided is a method wherein the suspending fluid is blood or blood mixed with some amount of another fluid. In some embodiments the fast-sedimenting particles are red and white blood cells, and the slow-sedimenting particles are platelets or other natural components of blood, such as proteins.

In certain embodiments of the technology, the slow-sedimenting particles are infectious organisms in the blood, such as bacteria, viruses, or other microorganisms. The slow-sedimenting particles could also be of non-biological origin, such as diagnostic or therapeutic polymer particles.

Also provided herein is a method wherein the slow-sedimenting particles are further concentrated after separation of the layer of fluid containing these particles.

Herein provided is a method for quickly separating, in less than 5 minutes, bacteria in blood from the majority of cells in blood, the bacteria being in very low concentrations, as low as 1 colony forming unit (CFU) per milliliter (mL).

Herein provided is a method according to the disclosed technology, wherein additives are placed in blood or other suspension to enhance the efficiency of recovery of the slow-sedimenting particles.

BRIEF DESCRIPTION OF THE SEVERAL VIEWS OF THE DRAWING

FIG. 5A shows a vertical cut-away view sliced through the axis of rotation. FIG. 5B shows a wedge-shaped slice of the same embodiment that has the primary lid [510] and upper lid [515] not shown for viewing convenience. The volume of the metered vestibule is defined by the position of an opening [572] in the wedge-shaped overflow baffle [571]. Also shown is the bowl [520], the slope [580], the trough [590], the connection to the rotating motor [525], the back wall of the vestibule [565], and the partially open primary lid [510] whose inward edge is positioned more inward that the weir [530]. The partially open upper lid [515] prevents overflowing blood from splashing out during rotation. If the vestibule [560] is overfilled, at the commencement of rotation the excess blood enters the overflow opening [572], flows down the overflow drain [573] and accumulates in the overflow chamber [566]. The balance of blood remains in the vestibule [560] and can be separated by sedimentation into a plasma layer and cell-pack layer.

DETAILED DESCRIPTION OF THE INVENTION

Introduction

Figure 1:
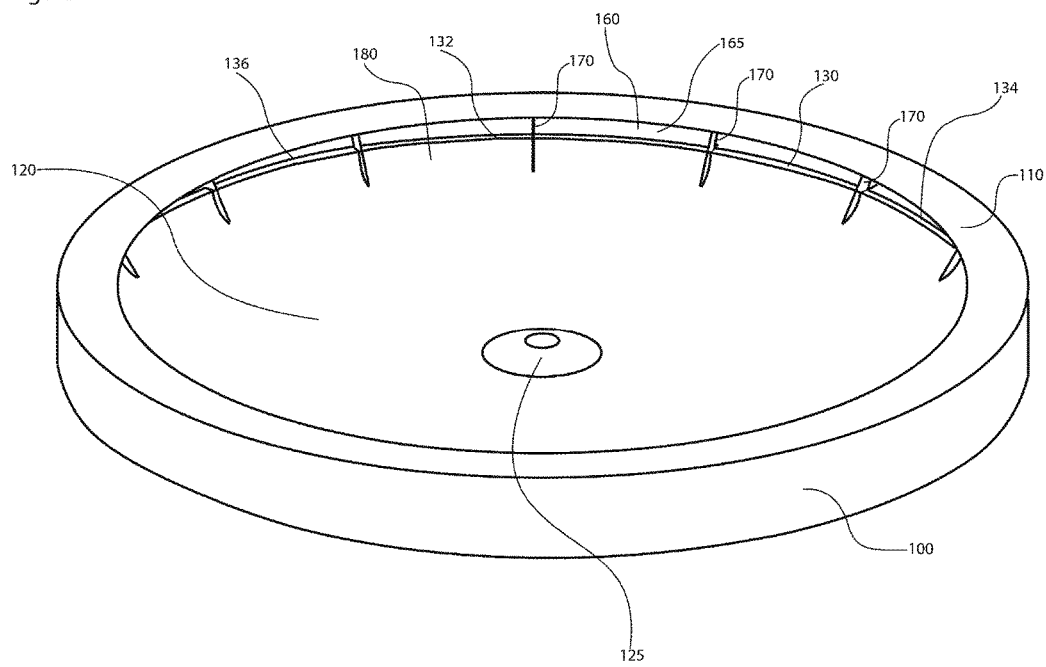
FIG. 1 depicts an illustration of a certain embodiment of a hollow device used in the method of this invention. In this illustration the view of a hollow device [100] presents several of the key features that assist in the separation of bacteria or particles from blood cells. Key features include a partially open lid [110] and a bowl [120]. The hollow cavity within the hollow device is defined by boundaries comprising the bowl, the back wall of the vestibule [165], and the imaginary extension of the partly open lid. Near the periphery of the hollow device, the bowl turns upward to the weir [130], which in this embodiment has a horizontal top [134]. The inward edge of the weir [132] connects to the top of the bowl [120], which top of the bowl is also called the slope [180] in this specification. The weir also has an outward edge [136] that connects to the trough, which trough is not shown in this view. During rotation, blood is spun into the cavity called the vestibule [160], forming a thick film of blood in a partly open channel in contact with the atmosphere. Also shown in this illustration are triangular baffles [170] that extend from the back wall of the vestibule to the slope of the bowl. In the center of the bowl is a connection [125] to a rotating shaft.

Provided herein is a method and system for rapidly separating slow-sedimenting particles from fast-sedimenting particles in a hollow rotating device. The rapid separation is accomplished one batch at a time by spreading the suspension over a large area within the hollow device, which creates a thick film of suspension. Rapid rotation of the hollow device creates relatively high sedimentation velocities for the particles; the differing sedimentation velocities cause the particles to separate themselves within the thick film. Finally the rotation is stopped to collect the fluid containing some of the slow-sedimenting particles while leaving the fast-sedimenting particles trapped inside the hollow device. The fast-sedimenting particles can also be recovered from the device. We start teaching our invention by discussing the difficulty of separating suspended particles, which is particularly difficult when the particles are similar in size and density. We then present the theory of separation by sedimentation and demonstrate the use of sedimentation to separate particles in at least one very significant application, using our novel and non-obvious technology.

Centrifugal Separation

We define centrifugation as the process of rotating a sample around an axis to generate a centrifugal force that operates on the particles and on the surrounding fluid. In contrast, the term sedimentation is defined as the process of moving particles through a liquid through the influence of an external field, such as a gravitational field, centrifugal field, electric field, etc. Herein a particle is defined as discrete quantity of heterogeneous or homogeneous matter, of any shape with characteristic size between 1 Angstrom and 1 mm, composed of gas, liquid or solid, or combinations thereof. Particle sedimentation can be produced by centrifugation, but is not limited to centrifugation. In the laboratory, centrifugation is a convenient method to produce sedimentation. Sedimentation velocity is defined as the velocity of the particle, relative to the surrounding fluid, during the sedimentation process.

Centrifugation processes have been commonly used to separate suspended particles of differing densities. For more than a century centrifugation in tubes has been used to separate blood into its various components (cells, platelets and plasma). In traditional laboratory work, the centrifugation time is sufficiently long that the particles move until they are separated into layers according to their density. We will refer to this as isopycnic (equal density) or equilibrium centrifugation in which all dynamic movement has stopped either because there is no more density difference to drive particles to move relative to each other and to the fluid, or because the particles have come to an impenetrable barrier such as the end of the test tube or to other immobile particles stacked up from the end of the tube or some other barrier. At the end of an isopycnic centrifugation process, all the particles will be separated serially in layers according to their densities, with the densest particles furthest from the axis of rotation.

With isopycnic centrifugation particles of equal density cannot be separated from each other, and particles with only slight density differences require a very long centrifugation time to arrive at isopycnic equilibrium.

Another common process for separating particles is filtration, a process in which particles smaller that the passageways (called pores) can pass, but particles larger than the passageways cannot pass. Filtration works well if the particles have sufficient differences in size and if the large particles do not block entrance of the small particles into the passageways.

Sedimentation

The novel sedimentation method for separating particles that we present in this invention can be applied to single batches or single volumes of particle suspension, volumes from 0.5 to 100 mL or more, processed in a batch in a single hollow device. There is minimal or no dilution of the suspension, so the waste fluid is minimized, an important aspect for some applications. The separation method can occur in less than 1 minute, even with large batches of suspension. Slowing the hollow device to collect the separated particles can be done in less than 5 minutes. The hollow device is not overly complicated or expensive, so it can be thrown away, thus precluding any cleaning that would be required for re-use of the hollow device.

The science behind our method is the fact that particles may sediment at different velocities, depending upon their size and their difference in density from the surrounding fluid; therefore they may be separable from each other during a dynamic sedimentation process produced by centrifugal spinning. Our method of spinning employs rotation of a hollow device that can be designed to accommodate large batches of suspension, large enough that even suspensions with very low concentrations of slow-sedimenting particles will provide enough numbers of particles for subsequent particle analysis.

Sedimentation occurs during centrifugation because the centrifugal force that causes movement of a particle in the fluid is balanced by the buoyancy force and drag force on the same particle. The centrifugal force is proportional to the particle density, and the buoyant force is proportional to the fluid density; so when these densities are not equal, these forces are not equal. Their imbalance creates a net accelerating force on the particle; however, the resulting acceleration and subsequent movement creates a drag force in the opposite direction, which drag force increases as velocity increases. Within seconds the particle reaches a velocity, relative to the fluid velocity, at which its centrifugal accelerating force is balanced by the drag and buoyant forces, and the particle continues to move until it encounters an immobile interface (a wall or another stationary particle), or it enters a fluid of the same or greater density, or the driving forces (centrifugal and gravity) on the particle is stopped. Small suspended particles are known to sediment in the Stokes flow regime when their particle Reynolds number is less than 0.1. The particle Reynolds number is defined as $Re_p = \rho_f v_s D_p / \mu$, where $D_p$ is the effective particle diameter, $\rho_f$ is the fluid density, $v_s$ is the sedimentation velocity, and $\mu$ is the fluid viscosity. The effective particle diameter is the diameter of a sphere having the same volume as the particle. In Stokes flow, the drag force, $F_D$, on the particle is given by Stokes law: $F_D=3\pi\mu D_p v_s$. A balance of the drag force, buoyant force and centrifugal force for a rigid sphere undergoing Stokes flow in a Newtonian fluid leads to the following equation for the sedimentation velocity:

$$v_s = \frac{D_p^2(\rho_p - \rho_f)(R\omega^2 + g)}{18\mu} \qquad \text{Equation 1}$$

where $\rho_p$ is the particle density, R is the rotational radius, $\omega$ is the rotational angular velocity, and g is the gravitational constant (which is often negligible compared to $R\omega^2$) (P. C. Hiemenz and R. Rajagopalan (1997) *Principles of Colloid and Surface Chemistry*, 3rd ed. New York: Marcel Dekker). In practice the actual sedimentation velocity is sometimes less than the theoretically predicted velocity because of interparticle interactions (such as collisions) and non-spherical shapes.

Our novel method of separating various particles in suspension is based upon these differences in sedimentation velocity. Whenever a mixture of particles comprises particles with different sedimentation velocities at least one particle will move at a different speed, irrespective of the number of particles present or the relative numbers of the faster sedimenting particles and the slower sedimenting particles. If only two types of particles are present the necessary condition for some separation to occur is that the ratio of the velocities of the fast-sedimenting and the slow-sedimenting particles be greater than unity. While this is necessary for separation, it may not be sufficient to retain separation, as the hollow device geometry and the deceleration play a large role in retaining separation and producing a separated product, as this document will show in the Examples.

In this invention the suspension of particles is placed in a hollow device and when the device is rotated the suspension is thrown outward, forming a thick film of suspension within a confined region of the device. The volume of the hollow device occupied by the suspension during spinning is called the "vestibule". This vestibule is shaped like a ring and contains fluid that is bounded on 3 sides by walls of the vestibule and is at least partly open on the inward side, with exposure to the atmosphere on this partly open portion of the vestibule. The open channel format differentiates this invention from other devices that separate suspensions such as blood in closed channels and narrow pathways. In embodiments that include a trough (see FIGS. 2-6), the inward surface of the vestibule is only partly open, as the inward side of the trough makes an enclosure on all sides of the suspension residing within the trough or the vestibule. We define "partly open channel" as a channel for containing the suspension during rotation that has between 10% and 100% of its inward-side area exposed to the atmosphere of the interior of the hollow device.

In this description of our invention, "film" is defined as a pool or volume of suspension or fluid whose thickness or depth is less than its width and less than its length. The term "thick film" is defined as a film of suspension having a thickness between 0.2 mm and 10 mm. Because the partly open channel may in some designs have different thicknesses within the film of suspension, the "average thickness" of the film is defined as a mean thickness of the film in the radial direction, averaged over the entire vestibule. The fast-sedimenting particles sediment faster than the slow-sedimenting particles, moving outward through the film toward the outward or "back wall" of the vestibule where they pile up into a "particle-pack", which is defined as a collection of fast-sedimenting particles at a higher concentration than originally existed in the suspension.

We teach the principles of sedimentation by first describing a field of uniformly sized spheres suspended randomly in a viscous fluid that is confined within solid boundaries. When some kind of force is applied to the particle, be it centrifugal, gravitational, electrostatic, magnetic or other, all the particles will start moving in concert. When the particle sizes and centrifugal forces are equal throughout the field, the particles will all move at the same velocity as long as Brownian motion is negligible and particles do not interact with each other. These particles, all moving in concert, will start to pile up when they encounter a solid impenetrable boundary at the end of the fluid field. Likewise on the opposite boundary of the fluid field there will be a clear section out of which the particles have moved. After a short time there are 3 sections to the field: (1) a section of higher particle density where the particles are piling up at the downfield impenetrable boundary, called a "particle-pack" layer; (2) a section that is cleared, or clarified, of particles located in the direction "upstream" from the direction of particle movement, called the "clarified layer"; and (3) a middle section that has the same particle density as in the original suspension. In this ideal case, there are distinct boundaries between these sections, which sections are identified by abrupt changes in the number density of suspended particles. With time the thickness of the particle-pack layer grows, as does the thickness of the clarified layer; but the length of the middle region decreases with time as the particles move into the particle-pack. Finally this middle region disappears entirely when all the particles have sedimented into the layer of particle-pack.

When the suspension contains many particles of slightly different size or shape or density, the sedimentation velocities of the particles will be slightly different. A clarified layer will exist, as will a particle-pack layer, but the boundaries will not be sharp and the density of the middle region will not be uniform. In systems with high initial particle density, collisions between particles will also contribute to making the boundaries indistinct.

In systems with very few particles, the same sedimentation will occur. Although it may be more difficult to observe a particle-pack layer and a clarified layer, these layers are defined and they still exist. A minimum system for the purposes of this invention consists of 1 slow-sedimenting particle and 3 particles that sediment at velocities faster than the slow-sedimenting particle. Upon sedimentation a majority of fast sedimenting particles finally forms a layer when 2 of the 3 fast sedimenting particles finally sediment to the downfield impenetrable boundary and form a particle-pack layer of fast-sedimenting particles of local higher particle density than in the original suspension. At this point the sedimentation process can be carefully stopped and the particle-pack layer separated from the balance of the suspension. For a random initial distribution of the particles, in some cases the slow-sedimenting particle will may also be in the particle-pack when the process is stopped. But on average for this 4-particle system, averaged over many experiments, the slow-sedimenting particle will not be in the particle pack as long as its velocity is slower than that of the 3 faster sedimenting particles. This principle is easy to envision because the average starting position of the slow-sedimenting particle is the center of the thick film, and the average position of the 3 faster sedimenting particles is also the center of the thick film, and on average 2 of 3 of the faster particles will arrive at the impenetrable boundary before the slow particle. As the numbers of particles increase above this minimum set, the probability of finding at least 1 slow-sedimenting particle outside of the fast-sedimenting particle-pack becomes very high very quickly.

In a system with two sets of large numbers of very different types of particles, each set of particles will sediment at its own velocity, with the fast-sedimenting particles forming their particle-pack most quickly, and the slow-sedimenting particles moving slowly into that particle pack. On the "upstream" side of the field, the fast-sedimenting particles will clear out quickly and the slow-sedimenting particles will clear out slowly. If the sedimentation is done for a long enough time, all the slow-sedimenting particles will eventually be cleared and will combine with the layer of particle-pack. However, if the sedimentation process is stopped before all the slow-sedimenting particles have sedimented into the particle-pack, the middle layer still contains the slow-sedimenting particles. Separation of the clarified layer and middle layer (containing the slow-sedimenting particles) from the particle-pack layer will provide fluid containing a number of slow-sedimenting particles, but few if any of the fast-sedimenting particles. If the sedimentation is stopped just as the last fast-sedimenting particle reaches the particle-pack layer, there will be a maximum number of slow sedimenting particles in the middle layer but no fast-sedimenting particles. However, if the process is stopped before the last fast-sedimenting particle reaches the particle-pack, separation of the layers will produce an even higher number of slow-sedimenting particles, but those particles will have a slight contamination by a small number of fast-sedimenting particles.

While the separation of particles appears fairly easy to accomplish, the more challenging aspect is the subsequent separation of the clarified layer and middle layer from the particle-pack layer. This might be done by skimming or draining one layer form another. However a skimming device is often complex. Part of our invention and method is the facile separation of the layer containing slow-sedimenting particles from the particle-pack. As is seen in the description and examples, this can be done passively by gravity when the different layers have different physical densities and when the hollow device is designed to accommodate separation and flow driven by gravity and density differences.

Bacteria and Blood

While the practice of various embodiments of this invention will find many applications, one significant and immediate application is a method for the separation of bacteria from blood. Table 1 presents some basic facts about blood components that are relevant to this method. A bacterium is defined herein as a single cell microorganism that has a cell wall, but lacks internal organization into a nucleus or organelles, and is classified by staining properties such as Gram-positive or Gram-negative or acid fast, or is classified by shape (rods, sphere, spiral, etc.) as known by those skilled in the art of microbiology. A microorganism is a replicating organism that can only be seen with the aid of a microscope, and includes, but is not limited to viruses, bacteria, protozoans, and certain algae and fungi.

There is a significant medical need for rapid identification of the species of bacteria in a blood infection and for rapid identification of the antibiotic resistance characteristics of the bacteria. In most analytical methods, the bacteria must be separated from the components of blood. We have found no reports of separating bacteria from blood components by isopycnic centrifugation of blood in tubes. Perhaps this is because, as Table 2 shows, the density range of bacteria overlaps the density range of red blood cells, thus rendering isopycnic separation of *Escherichia coli* (*E. coli*) bacteria from blood impractical. Many other species of bacteria have the same range of densities and would have similar difficulty of separation by isopycnic centrifugation.

TABLE 1

Some properties of major human blood components

| Component | Concentration [#/mL] | Size [μm] | Density [g/mL] | Comments |
|---|---|---|---|---|
| Red blood cell | $4.0\text{-}5.7 \times 10^9$ | 6.2-8.2 | 1.086-1.122 | Usually enucleate; generally no DNA; flexible biconcave discoid shape. |
| White blood cell | $4\text{-}11 \times 10^6$ | 7-30 | 1.092 | DNA in every cell; spherical with many different sizes; monocytes can be as large as 30 μm. |
| Platelets | $1.3\text{-}4.0 \times 10^8$ | 2.0-4.0 | 1.072-1.077 | No DNA; easily activated to aggregate and adhere to surfaces; biconcave discoid when not activated. |
| Plasma | N/A | N/A | 1.024 | Contains high concentrations of proteins and other biomolecules. |

TABLE 2

Relative sedimentation properties of blood component and bacteria

| Component | Density range (g/cm³) | Density used for calculation (g/cm³) | Nominal size used for calculation (μm) | Relative Velocity* |
|---|---|---|---|---|
| Red blood cell | 1.086-1.122 | 1.098 | 8 | 30 |
| While blood cell | 1.092 | 1.092 | 15 | 96 |
| Platelet | 1.072-1.077 | 1.077 | 3 | 3 |
| E. coli | 1.08-1.10 | 1.095 | 1.5 | 1 |

*Relative to E. coli (modeled as 1.095 g/cm³, 1.5-μm sphere) calculated using the nominal values in the table and a plasma density of 1.024 g/cm³. RBCs, WBCs and platelets were also modeled as spheres with diameters given above.

Blood is defined as a natural body fluid that is a mixture of (1) a liquid phase called plasma that is an aqueous solution of salts, proteins, and other small organic and inorganic molecules, and (2) formed components including platelets, red blood cells, and many types of white blood cells. The composition and properties of blood and blood components are known to those in the art of medicine and physiology.

The rising prevalence of antibiotic resistance in bacterial pathogens is a significant threat to global health. Life-threatening bloodstream infections caused by antimicrobial-resistant bacteria are a tremendous burden on healthcare and lead to much higher patient treatment costs, increased length of hospitalization, and most importantly, higher rates of morbidity and mortality. Few new antibiotics are in development to treat these pathogens, leaving physicians with fewer choices to treat these increasingly resistant organisms. The most concerning relevant Gram-negative pathogens include *Klebsiella pneumoniae, Escherichia coli (E. coli)*, and members of the genus *Enterobacter*. The carbapenem class of antibiotics has been used as a last-resort against members of the Enterobacteriaceae, inevitably leading to the generation and spread of resistant strains, called carbapenem-resistant Enterobacteriaceae (CRE). Infections with these bacteria have produced mortality rates as high as 50% (G. Patel, S. Huprikar, S. H. Factor, S. G. Jenkins, and D. P. Calfee (2008) "Outcomes of carbapenem-resistant *Klebsiella pneumoniae* infection and the impact of antimicrobial and adjunctive therapies," *Infection Control & Hospital Epidemiology*, 29, 1099-106) and they have been associated with significant outbreaks. Of the Gram-positive pathogens, *Staphylococcus epidermidis* and *S. aureus* are often associated with bacteremia and bloodstream sepsis, but usually have lower mortality rates (S. Kleinschmidt, F. Huygens, J. Faoagali, I. U. Rathnayake, and L. M. Hafner (2015) "*Staphylococcus epidermidis* as a cause of bacteremia," *Future Microbiology*, 10, 1859-79). Resistance characteristics of both Gram-positive and negative bacteria are a growing concern.

The gold standard of profiling antibiotic resistance has long been based on phenotypic assays; however, these tests require a relatively long turnaround time, usually at least 12-24 hours, between sample acquisition and assay reporting (D. J. Diekema and M. A. Pfaller (2013) "Rapid detection of antibiotic-resistant organism carriage for infection prevention," *Clinical Infectious Diseases*, 56, 1614-20). Even recently approved molecular techniques for bloodstream infections, designed to diagnose the organism and its antibiotic resistance profile, require a positive blood culture before the resistance assay can be performed. Without detailed information on both the infecting bacterium and its resistance profile, clinicians cannot reliably determine the most effective antimicrobial treatment.

The need to rapidly identify and initiate treatment of bloodstream infection becomes critical if the infecting organism is resistant to the initially applied antibiotic treatment. Survival rates drop by as much as 7.6% per hour as effective treatment is delayed, giving urgency to rapid identification of antimicrobial susceptibility profiles (A. Kumar, D. Roberts, K. E. Wood, B. Light, J. E. Parrillo, S. Sharma, R. Suppes, D. Feinstein, S. Zanotti, L. Taiberg, D. Gurka, A. Kumar, and M. Cheang (2006) "Duration of hypotension before initiation of effective antimicrobial therapy is the critical determinant of survival in human septic shock," *Critical Care Medicine*, 34, 1589-96).

The exact threshold for clinical symptoms of infection is unclear and may depend on species, but certainly at levels as low as 10 CFU/mL, sepsis becomes a threat (P. Yagupsky and F. S. Nolte (1990) "Quantitative aspects of septicemia," *Clinical Microbiology Review*, 3, 269-79). The current clinical identification process employed for suspected septicemia typically requires at least 24 hours, as a sample must be grown in culture before additional evaluation can identify the infecting species and determine its antibiotic resistance profile. Such evaluation is performed by a variety of techniques known to those skilled in the art, including phenotypic assays, fluorescence in situ hybridization, mass spectrometry, and polymerase chain reaction (PCR). PCR methods carry the possibility of multiplexed assays and high levels of sensitivity, allowing rapid pathogen detection and characterization. However, blood has proven to be a particularly difficult medium for PCR analysis, as blood contains endogenous inhibitors that decrease the efficiency of the amplification step through interference with the polymerase or interaction with the DNA itself (J. Hedman and P. Radstrom (2013) "Overcoming Inhibition in Real-Time Diagnostic PCR," in *PCR Detection of Microbioal Pathogens*, vol. 943, *Methods in Molecular Biology*, M. Wilkes, Ed.: Springer, pp. 17-48). Thus PCR methods could be better employed if the bacteria were separated from the blood components.

In addition to PCR, rapid nucleic-acid-based tests may have sufficient sensitivity to identify the bacteria species and the resistance profile directly from the bacterial DNA, without amplification of the bacteria (culturing the bacteria) or amplification of certain DNA sequences (PCR techniques). These nucleic-acid-based tests usually involve hybridization between a unique DNA sequence and a complementary DNA sequence attached to a marker, the sequence unique to the bacteria or to the resistance gene. Thus only when the target DNA is present does the hybridized marker produce signal. There are several such technologies known to those skilled in the art.

In these and other identification assays, there remains a need to separate the bacteria from the blood, since blood cells, blood proteins and even the human DNA from white blood cells may interfere with the sensitivity of these hybridization techniques that must operate on low copy numbers of DNA.

As a non-limiting example of a process to separate bacteria from whole blood, a process may include filtering the bacteria-laden blood through a filter with pore a pore size larger than the bacteria but smaller than the blood cells; however the very large numbers of red and white blood cells in a blood sample to be filtered will quickly block the pores of the filter and make separation of bacteria very difficult if not impossible because flow through the filter will stop due to clogging.

In another non-limiting example, analysis of the DNA of the bacteria may be complicated or impeded by the presence of white blood cells or by the presence of DNA from WBCs; thus adequate separation of WBCs from bacteria is beneficial and often necessary.

This patent application presents a novel method with which very low concentrations of bacteria may be rapidly separated from blood. Although 100% efficiency of bacterial recovery is not required for these nucleic-acid-based analyses, high collection efficiency is desired, as higher collection efficiency will provide more bacterial genomic material for the analysis.

In the clinic or hospital, blood samples from infected patients are often obtained in 2 to 10 mL increments in vacutainer tubes. Multiple tubes can be collected from a patient to increase the total amount of blood and total number of bacteria collected for analysis. It is desirable for bacterial separation to be done in 60 minutes or less to reduce the total time for identification of the bacteria and its resistance profile. It is more desirable to separate bacteria in 15 minutes or less. Even more desirable and truly remarkable is to separate bacteria from blood in 5 minutes or less, particularly when the bacterial concentration is less than 100 CFU/mL.

Another desirable aspect is to reduce as much as possible the total fluid volume used in the separation process. Those separation processes that require or that generate large volumes of waste fluid are less desirable as the fluid is contaminated with human blood pathogens and must be carefully handled and disposed of to protect health-care workers. Preferred separation processes have minimal dilution of the blood with other fluids.

Perhaps the largest challenge in separating bacteria from blood is the extremely high concentration of red blood cells (RBCs), which can outnumber the bacteria by nearly one billion to one. Platelets are another complication as they are very easily activated to aggregate to each other or to adhere to surfaces of the device. Even when the blood is anticoagulated by treatment with calcium chelators such as sodium citrate or ethylenediaminetetraacetic acid (EDTA), the platelets still tend to stick to some surfaces. As mentioned, contamination by WBCs is a problem when the subsequent analysis of bacteria involves DNA identification because high numbers of white cells will contribute human DNA that can interfere with or compete with bacterial DNA analysis.

Both RBCs and WBCs have ranges of sizes and densities. For purposes of calculations and comparisons used in this application, we have defined an "average red blood cell" as a discoidal envelope with diameter of 8 μm and average thickness of 2 μm, containing a volume of 90 femtoliters, and having a density of 1.098 g/cm$^3$.

The Method of Sedimentation in a Hollow Device Using Blood

In the case of bacteria and blood cells in blood, the sedimentation velocities are often slower than predicted because RBCs and most enteric bacteria are not spherical, blood is not a Newtonian fluid, and the particles collide with each other. Nevertheless, Equation 1 gives a fairly good estimate of sedimentation velocities, as the correction factors for spheroids are not large (P. C. Hiemenz and R. Rajagopalan (1997) *Principles of Colloid and Surface Chemistry*, 3rd ed. New York: Marcel Dekker) and blood plasma is nearly Newtonian at the low shear rates generated during sedimentation (D. O. Cooney (1976) *Biomedical Engineering Principles*, vol. 2. New York: Marcel Dekker). Although experiments are needed to determine exact sedimentation velocities, Equation 1 is very useful in examining how particle size and particle density will produce relative differences in sedimentation velocity. The deviations from the sedimentation velocities predicted by Equation 1 are similar for all blood components listed in Table 1, and so by calculating the ratios of velocities, the non-ideal corrections nearly cancel out each other. Table 2 gives the ratio of sedimentation velocities of the blood cells, ratioed to the sedimentation velocity of an *E. coli* bacterium, modeled as a sphere. By these simple calculations, a 15-μm WBC will have a sedimentation velocity about 96 times faster than *E. coli*, and a RBC will have a sedimentation velocity about 30 times faster than *E. coli*. Platelets move about 3 times faster than *E. coli*.

Because blood cells are deformable, they pack together and squeeze out much of the plasma from the cell-pack. Meanwhile the bacteria sediment 30 times slower than the RBCs, and by the time that nearly all RBCs have collected in the cell-pack, the bacteria have only moved partway towards the cell-pack and many bacteria are still in the plasma layer. The hollow device is carefully slowed to a stop, to avoid remixing the plasma layer with the cell-pack layer. As the hollow device slows to a stop, gravity pulls the less dense plasma to one region of the hollow device, and gravity pulls the more dense cell-pack to another region, thus separating the cell-pack from the plasma, which plasma contains bacteria that did not sediment into the cell-pack. Because bacteria also sediment, but more slowly, it is inevitable that some bacteria will sediment from plasma into the cell-pack and not be recovered when the plasma is collected. Additionally the initial random distribution of bacteria in the blood spun into the vestibule will place some bacteria close to the back wall of the hollow spinning device where the first amount of cell-pack forms; these have extremely low probability of escaping from the cell-pack and they will rarely be recovered. Thus 100% recovery of bacteria is not possible with this method. Nevertheless, as we will show in some examples, a high percentage of the bacteria in blood can be recovered, and this high recovery, coupled with short processing time and high processing volume, makes this method very useful for many applications where rapidity and high numbers of bacteria from blood are important.

As one skilled in the art knows, the thickness of the cell-pack layer grows as the spinning time increases, up until the time when all of the RBCs and WBCs have sedimented into the cell-pack. The cell-pack may continue to consolidate with more spinning time, as plasma is squeezed out, but during any additional spinning time more bacteria sediment out of the plasma and collect in the cell pack and are not easily recovered. The hematocrit represents the volume percentage of blood cells in blood, and thus when the cell pack is finally formed, we expect that the percentage of the thick film in the vestibule that is cell-pack will at most be represented by the hematocrit of the blood suspension. If the blood was diluted before spinning by adding diluent or adenosine diphosphate (ADP) solution or by spiking with bacteria, then the percentage of vestibule thickness occupied by cell-pack will be less than the blood cell volume fraction of the donor. The normal hematocrit for males is 39-50 and for females is 35-45. Some patients may have low hematocrit due to disease. In some cases of disease and when blood is combined with diluent, the consolidated cell-pack layer may be as thin as 1/10 of the vestibule thickness.

It is important to separate the majority of RBCs and WBCs from the recovered plasma, as too many RBCs and WBCs would clog a subsequent filtration processes used to concentrate the bacteria. In this specification, the majority of RBCs is defined as more than half of the RBCs; the majority of WBCs is defined as more than half. The exact number of RBCs and WBCs necessary to clog a filter depend on the type of filter and the pore size. The number of cells required to clog a filter will also depend on the filter type. Membrane filters come in various forms and materials, including woven or non-woven polymers or cellulosics, track-etched polymers, coagulated polymer, and expanded polymers, as is known to those skilled in the art of separation technology. We have found that more than half of the RBCs must be removed to filter the recovered plasma using polysulfone membrane filters of 0.45 μm nominal pore size. As mentioned previously, it is essential to remove nearly all WBCs if the subsequent analysis of the bacteria compromise DNA recognitions techniques, as the WBCs will contaminate the bacterial sample with human DNA. We believe that proper embodiments of this method do remove more than 99% of the WBCs, based on the observation that we have never seen a WBC in the hundreds of micrographs taken of the separated plasma.

As will be taught, various embodiments of this method can use hollow devices of many shapes—spherical, conical, discoidal, or combinations thereof—as long as they are balanced so they can be spun at high rotational velocity with minimal wobble.

Background on Related Separation Methods for Blood

As background to this application, we will briefly present previously reported methods of separating blood components in non-hollow disks, and separating bacteria from blood.

Centrifugal Disks.

There are several reports of centrifugal disk separation processes in which microliter quantities of blood are placed within a chamber built into a solid disk the size of a compact disk (CD) or digital video disc (DVD); then the disk is spun on a motor similar to those used in a CD or DVD player. In most cases after equilibrium centrifugation has thoroughly separated plasma from the cellular components, the separated plasma flows further downstream on the disk toward a diagnostic process. To our knowledge, these batchwise centrifugal microfluidic processes have not yet been used to differentially separate low concentrations of bacteria from blood, most probably because these devices process very small quantities of blood. Furthermore these devices are not hollow, as a hollow device is defined herein as a device having a contiguous open space of size greater than 20 mL within the confines and boundaries of the device.

An example of a non-hollow device was published by Haeberle et al in which whole blood was deposited into a 5-μL metered chamber (S. Haeberle, T. Brenner, R. Zengerle, and J. Ducree (2006) "Centrifugal extraction of plasma from whole blood on a rotating disk," *Lab on a Chip*, 6, 776-81). When the disk was spun, the centrifugal force pushed the blood past a hydrophobic stop and down a long microfluidic channel whose cross section and length control the time required to empty the metered chamber. Sedimentation created a red cell concentrate that flowed down the channel from the metered chamber into the first collection chamber and filled it, with some plasma on top. After the cell-pack exited the metered chamber, the plasma flowed from the metered chamber into the first collection chamber. Eventually the plasma spilled over from the first collection chamber into the plasma collection chamber. While this device separated plasma from cell-pack using centrifugal forces, the method was never demonstrated to separate bacteria from blood, and the method does not use a hollow device to process at least 0.5 mL of blood.

Amasia et al. have also designed a microfluidic system on a spinning solid disk that separates larger batches of blood. (M. Amasia and M. Madou (2010) "Large-volume centrifugal microfluidic device for blood plasma separation," *Bioanalysis*, 2, 1701-10) This device is described in U.S. Pat. No. 9,186,672, which is included herein by reference. In this device there is no drain channel, and the plasma and cell-pack separate while remaining in the enclosed chamber in which the blood was placed.

In general these prior spinning disk devices differ significantly from the present invention because the separation occurs in small volumes in enclosed chambers and enclosed microfluidic channels, while in the present invention the entire sample of blood is in a thick film in a contiguous open vestibule, and not confined within small chambers and microchannels. A differentiating aspect of our invention is the partly open and wide channel in which a large volume of blood resides. Thus the thickness in the radial direction of our partly open channel is less than the width of the vestibule in the vertical direction and much less than the circumferential length of the vestibule.

Batchwise blood separation methods, such as those prior technologies described above and our novel method described herein, use discrete and separate volumes of blood and thus differ from continuous separation methods in which a continuous flow of blood, sometimes joined with other fluids, is processed to separate and produce 2 or more continuously flowing streams of separated components.

Bacterial Migration in Microfluidic Channels.

The process of pumping bacteria-laden blood through straight, branched, or curved channels has been successfully applied to separate bacteria from diluted blood at very slow flow rates. There have been several observations that when blood flows in narrow channels, the RBCs tend to migrate away from the channel wall (P. Pranay, R. G. Henriquez-Rivera, and M. D. Graham (2012) "Depletion layer formation in suspensions of elastic capsules in Newtonian and viscoelastic fluids," *Physics of Fluids*, 24, 61902, 1-30). This is called "margination", as it leaves a margin of fluid near the wall with a lower RBC concentration. This occurs in any size of channel, but is more easily observed in small channels because the fraction of the cell-depleted volume is greater than the fraction of the cell-depleted volume in larger channels. Many interesting rheological phenomena have been attributed to the migration of RBCs away from the wall, such as the Fahraeus effect (the hematocrit in very small tubes is less than that of the supply reservoir) and the Fahraeus-Lindqvist effect (the apparent viscosity of blood decreases as the tube diameter decreases) (R. Skalak and S. Chien (1986) *Handbook of Bioengineering*. New York: McGraw Hill.). The other components of blood do not migrate away from the walls to the same extent as the RBCs, and this becomes a point of exploitation for separation of blood components in narrow channels.

The centric migration of RBCs in straight narrow tubes tends to push the other blood components (including bacteria) toward the walls. This is a type of particle focusing, although in reality there is a rather diffuse boundary to the "focused" volume of particles.

Particles can also be focused in straight or curved channels by virtue of the balance between "lift" forces (forces pushing away from the wall), centripetal forces, and linear inertial forces that act more strongly on denser and more massive particles. There are many publications in this area, and several devices have been developed that employ pumping of diluted blood in narrow straight or curved channels to focus microparticles (D. Di Carlo (2009) "Inertial microfluidics," *Lab on a Chip*, 9, 3038-3046).

For example, Hou et al. took advantage of RBC migration away from the walls in small rectangular channels to preferentially concentrate bacteria near the walls. This was done using a suspension of bacteria mixed with washed blood cells, which blood cells were resuspended at a hematocrit of 45 (H. W. Hou, H. Y. Gan, A. A. Bhagat, L. D. Li, C. T. Lim, and J. Han (2012) "A microfluidics approach towards high-throughput pathogen removal from blood using margination," *Biomicrofluidics*, 6, 24115-24115, 1-13). The red cells were marginated over a length of several mm; then the channel was expanded and two side-stream bifurcations drew off flow from the RBC-depleted region at the periphery of the wide channel. The central section of blood was directed to a second narrow channel, marginated again, expanded, and the RBC-depleted layer skimmed a second time. Using washed human blood spiked with *E. coli* or *S. cerevisiae*, the microbial separation efficiency was about 80% for the 2-stage process. However, an estimated 80% of the WBC and platelets were also recovered with the bacteria. Thus for genomic identification of the bacterial species, a second separation process would be needed to remove the WBCs to preclude sample contamination by human DNA. The report indicated that there were problems with high pressure-drops and leakage at flow rates greater than 15

μL/min. Scaling up to mL volumes would present a manufacturing challenge to produce a leak-proof single device with multiple flows in parallel. For example, to process 7 mL of blood in 9 minutes at 15 μL/min would require 52 channels in parallel. An advantage of this method is that whole (undiluted) blood can be used.

Mach and Di Carlo (A. J. Mach and D. Di Carlo (2010) "Continuous scalable blood filtration device using inertial microfluidics," Biotechnol Bioeng, 107, 302-11) used lift forces to move RBCs toward microchannel walls and margination forces to move them away from the walls, which focused dilute RBCs in a suspension of bacteria. After 4 mm of flow length, the channel was expanded gradually to 160 μm×20 μm and the RBCs remained focused near the wall. The RBCs were then drawn off through side channels leaving the bacterial suspension in the middle of the channel. Drawing off the RBCs removed about 88% of the RBCs (in the first stage), but also removed some bacteria. As in the previous example, two stages of separation were employed, and this device was built into a massively parallel system with 40 two-stage channels that could process 8 mL/min of diluted blood. However, the processed blood had been diluted 1/200 with a sodium chloride solution containing E. coli, so this represents only about 40 μL/min of whole blood in 40 channels, or about 1 μL/min of whole blood per channel. The bacterial concentration was rather high, at $10^8$ CFU/mL, but 80% of the bacteria were recovered. While this is a very good recovery, the processed volume is tremendously large (7 mL blood would become 1.4 L of total fluid) and it would require 25 of these massively parallel systems to process 7 mL of whole blood in 7 minutes.

Patent documents related to separation in spiral and straight microchannels are plentiful. Two patents related to our technology are U.S. Pat. No. 8,208,138 B2 by Papautsky et al., and US20130306566 A1 by Mao et al., which are incorporated herein by reference.

In an application of inertial microfluidics, Wu et al. separated E. coli mixed into human blood using a flow system in which the diluted blood was sheathed with another fluid flow (to protect from cells hitting the wall) and then deflected by an "acting" flow (Z. G. Wu, B. Willing, J. Bjerketorp, J. K. Jansson, and K. Hjort (2009) "Soft inertial microfluidics for high throughput separation of bacteria from human blood cells," Lab on a Chip, 9, 1193-1199). These impinging flows changed the fluid and particle momentum twice. The more massive blood cells were deflected further than bacteria, leading to a separation and collection of the bacteria. While the separation was not perfect (there were some bacteria in the red blood cells and vice versa), the bacteria were focused and collected at a 300-fold enriched concentration. There was no mention of platelets or white blood cells. While this technique has great potential for small flows on a chip, the flow rate was only 18 μL/min, and there are additional large volumes of fluid involved. For example, in these experiments the final dilution of the blood was from 1:500 to 1:1000, mostly due to the "sheath" and "acting" flows that produced the focused stream of bacteria. While this process had good separation and actually concentrated the bacteria, it might be less practical to use this process on significant quantities of blood in short times because the large dilutions require large fluid volumes and produced more waste fluid. Separation by sheath flow is also described in U.S. Pat. No. 9,470,618 B2 by Farrell et al. and is incorporated herein by reference.

Chemical Capture for Separation.

Bacteria have been efficiently separated from blood using chemical capture of the bacteria onto beads and other surfaces. The governing principle for chemical capture of a bacterium is that a physical or chemical interaction attaches the bacterium to a particle or surface that is more easily separated from the blood than the bacterium alone could be separated. While many types of separation could be used, in current practice magnetic bead and packed column separations are more prevalent.

One of the requirements for chemical capture of a yet-unidentified bacterium is that the capturing agent must be fairly non-specific to the bacterial species so it can attach to every kind of bacterium, but simultaneously have no or very minimal interaction with the human blood components, including blood proteins that may block the binding sites. While certain species or classes of bacteria may have specific antigens that could be bound by complementary antibodies, what is more advantageous is some chemical group that is present on all bacteria, and yet is absent from all mammalian cells. Although no such chemical group is yet reported, humans possess an immune system protein called mannose binding lectin (MBL) in their blood that binds to the surface of all of the clinical pathogens of interest in most antibiotic resistance situations, including Enterococcus ssp., Klebsiella spp., E. coli, S. aureus, S. pneumonia, S. pyogenes, P. aeruginosa, and many other bacteria, viruses, fungi and some protozoa (O. Neth, D. L. Jack, A. W. Dodds, H. Holzel, N. J. Klein, and M. W. Turner (2000) "Mannose-binding lectin binds to a range of clinically relevant microorganisms and promotes complement deposition," Infection and Immunity, 68, 688-693). This lectin and parts thereof have been used to capture and separate bacteria from blood (J. H. Kang, M. Super, C. W. Yung, R. M. Cooper, K. Domansky, A. R. Graveline, T. Mammoto, J. B. Berthet, H. Tobin, M. J. Cartwright, A. L. Watters, M. Rottman, A. Waterhouse, A. Mammoto, N. Gamini, M. J. Rodas, A. Kole, A. Jiang, T. M. Valentin, A. Diaz, K. Takahashi, and D. E. Ingber (2014) "An extracorporeal blood-cleansing device for sepsis therapy," Nature Medicine, 20, 1211-1216). This construct of a lectin is also described in U.S. Pat. No. 9,150,631 B2 by Super et al. and is incorporated herein by reference.

Another useful molecule is Zn-dipicolylamine, an organic molecule much smaller than a lectin, which is reported to bind to many species of bacteria (W. M. Leevy, J. R. Johnson, C. Lakshmi, J. Morris, M. Marquez, and B. D. Smith (2006) "Selective recognition of bacterial membranes by zinc(II)-coordination complexes," Chemical Communications, 1595-1597). It displays minimal binding to mammalian cells (M. Gao, Q. L. Hu, G. X. Feng, N. Tomczak, R. R. Liu, B. G. Xing, B. Z. Tang, and B. Liu (2015) "A Multifunctional Probe with Aggregation-Induced Emission Characteristics for Selective Fluorescence Imaging and Photodynamic Killing of Bacteria Over Mammalian Cells," Advanced Healthcare Materials, 4, 659-663) and thus has been used to capture bacteria from blood (J. J. Lee, K. J. Jeong, M. Hashimoto, A. H. Kwon, A. Rwei, S. A. Shankarappa, J. H. Tsui, and D. S. Kohane (2014) "Synthetic ligand-coated magnetic nanoparticles for microfluidic bacterial separation from blood," Nano Lett, 14, 1-5). Zn-dipicolylamine is reported to become associated with anionic phospholipids on the surfaces of Gram-negative and Gram-positive bacteria. Bacterial capture by magnetic beads attached to Zn-dipicolylamine is also described in US20140212335 A1 by Lee et al. and is incorporated herein by reference.

The biopolymer heparin sulfate (HS) appears to bind some bacteria. HS is found on the surface of many mammalian cells, and apparently some bacteria have developed a binding affinity for HS, including some species of *Heliobacter, Staphylococcus, Streptococcus, Pseudomonas, Escherichia*, and *Mycobacterium*. Some types of antibiotics (e.g., vancomycin, daptomycin, polymixin B) are used for bacterial capture, but it is unproven if these antibiotics have general affinity for all bacteria (Y. W. Chu, D. A. Engebretson, and J. R. Carey (2013) "Bioconjugated Magnetic Nanoparticles for the Detection of Bacteria," *Journal of Biomedical Nanotechnology,* 9, 1951-1961).

Some examples of bacterial capture use superparamagnetic (SPM) beads that have a useful magnetic property in that they are negligibly magnetic in the absence of a strong magnetic field (so they do not stick to each other), but become magnetic in the presence of a strong field and are easily captured by a magnet. SPM beads are usually made of iron oxide or manganese oxide, and are quite small, often having a size on the order of 10 to 100 nm. They can be purchased with "ready-to-conjugate" surface chemistry, so they can be easily attached to biomolecules (J. S. Beveridge, J. R. Stephens, and M. E. Williams (2011) "The Use of Magnetic Nanoparticles in Analytical Chemistry," *Annual Review of Analytical Chemistry, Vol* 4, 4, 251-273).

One application of bacterial capture and separation is the "artificial spleen" developed by Kang et al. (J. H. Kang, M. Super, C. W. Yung, R. M. Cooper, K. Domansky, A. R. Graveline, T. Mammoto, J. B. Berthet, H. Tobin, M. J. Cartwright, A. L. Watters, M. Rottman, A. Waterhouse, A. Mammoto, N. Gamini, M. J. Rodas, A. Kole, A. Jiang, T. M. Valentin, A. Diaz, K. Takahashi, and D. E. Ingber (2014) "An extracorporeal blood-cleansing device for sepsis therapy," *Nat Med,* 20, 1211-1216). Genetic manipulation produced a molecule with the ligating end of mannose binding lectin attached to the Fc fragment of IgG. The Fc end of the construct was bound to 250-nm SPM beads. When injected into the blood stream of a living rat, *E. coli* and *S. aureus* were surrounded by these beads and were collected from whole blood through a porous barrier toward magnets and then discarded, while the whole blood was returned to the rat. A clearance of about 90% of the bacteria from whole blood was reported when the bacterial load was about $10^4$ CFU/mL.

In an in vitro model using bovine blood spiked with *E. coli*, Lee et al. used SPM beads coated with bis-Zn-dipicolylamine (J. J. Lee, K. J. Jeong, M. Hashimoto, A. H. Kwon, A. Rwei, S. A. Shankarappa, J. H. Tsui, and D. S. Kohane (2014) "Synthetic ligand-coated magnetic nanoparticles for microfluidic bacterial separation from blood," *Nano Letters,* 14, 1-5). In a non-flowing system, a first separation removed 70% of the bacteria from diluted blood (1:50), and a second separation was reported to remove all the remaining bacteria. Using whole blood in a flow system at 1 mL/min, about 80% of the *E. coli* was cleared in one pass, and a second pass boosted the clearance to 90-95%. The authors suggested that there was some non-specific binding of red blood cells to the SPM beads.

Heparin-coated beads in a column were used successfully to remove about 60% of *S. aureus* from buffer solution in vitro (I. Mattsby-Baltzer, T. Bergstrom, K. McCrea, R. Ward, L. Adolfsson, and O. Larm (2011) "Affinity apheresis for treatment of bacteremia caused by *Staphylococcus aureus* and/or methicillin-resistant *S. aureus* (MRSA)," *Journal of Microbiology & Biotechnology,* 21, 659-664). The adsorbed bacteria were then eluted with a 2M NaCl solution. Whether this would work in whole blood is unknown.

Of course, antibodies that bind bacteria could be used as ligands. However, antibodies are usually very specific, and unless one already knows the species of the blood pathogen, employing antibodies to bind to bacteria would probably be an inefficient approach as many and various types of antibodies would need to be simultaneously employed to evaluate an unknown clinical blood infection. One possibility is to use antibodies to the lipopolysaccharides found on the outer membrane of Gram-negative bacteria, as this would provide chemical binding to a group of bacteria.

For example Wang et al. used various antibodies attached to glass to capture *E. coli* from whole blood (S. Q. Wang, F. Inci, T. L. Chaunzwa, A. Ramanujam, A. Vasudevan, S. Subramanian, A. C. F. Ip, B. Sridharan, U. A. Gurkan, and U. Demirci (2012) "Portable microfluidic chip for detection of *Escherichia coli* in produce and blood," *International Journal of Nanomedicine,* 7, 2591-2600). The use of an antibody to lipopolysaccharide binding protein, along with the lipopolysaccharide binding protein (which bound to the *E. coli*) was best able to capture *E. coli* by binding to a glass surface. Up to 70% binding efficiency was measured, and limits of detection were down to 50 CFU/mL. However this was a batch process that required at least 3 hrs to bind the *E. coli* and then wash out the blood.

In summary, none of these reported methods to separate low concentrations of bacteria from blood are ideal for rapid separation of low concentrations of bacteria from large volumes of blood. The microfluidic devices processes quantities much less than 10 mL of blood, and so the devices would have to be built in a manifold parallel system to separate the bacteria from blood in less than 10 minutes. Chemical capture methods lack the non-specificity to capture any species of bacteria that might be in blood. Most of these methods require diluted blood, and thus generate large amounts of waste.

Sedimentation Method of Separating Bacteria from Blood

Our novel and useful method of separating bacteria from blood employs an open hollow device in the shape of a hollow disk or hollow sphere or hollow cone or other hollow shape. The word "hollow" as used in the application does not imply that the interior volume is enclosed by a continuous solid surface, as in most cases there is an opening, wide or small, in the upper part of the hollow device through which a pipette can be inserted. The word "disk" as used in this application refers to a general shape of a flattened spheroid, and does not imply or require that the upper or lower surfaces are flat or are parallel. In most hollow devices that we have made, the bottom of the device is curved to various extents to allow drainage of plasma, to accommodate placement on the spinning motor, and to reduce the total amount of material used to construct the hollow device. In some embodiments of hollow devices there is a hole or drain in the bottom surface of the hollow chamber through which the plasma may exit following separation.

The purpose of this invention is to separate bacteria from large quantities of blood in a rapid manner. It is not necessary for the bacterial separation to be perfect, but it is most desirable for an imperfect separation to be rapid and still provide a sufficient quantity of bacteria in a clean plasma, sufficiently cleared of red and white blood cells, for use in a subsequent process.

Preparation of Blood

In the examples and descriptions of embodiments of the methods used to separate bacteria from blood, the blood is collected from human volunteers into commercial anticoagulant-containing vacutainer tubes according to approved protocol at Brigham Young University. The tubes of anticoagulants are sodium citrate (BD #369714, Becton Dickinson, Franklin Lakes, N.J.), EDTA (BD #366643) and sodium heparin (BD #367874). Other types of anticoagulants and types of collection tubes may be used, as known by those skilled in the art of clinical blood collection. Concentrations of anticoagulants may be varied to prevent platelet activation or blood coagulation as needed and as know by those skilled in the art. The blood is processed on the same day as collection. To simulate a blood infection, just before spinning in a hollow device, blood from a vacutainer is placed in a vial and then spiked with a small volume of *E. coli* suspended in phosphate buffered saline (PBS), and the vial is inverted several times by hand or is lightly vortexed to produce a desired concentration of bacteria in the blood used in the experiments.

Various additives can be added to the blood before it is processed. As mentioned for research and development purposes, a very small amount of bacterial suspension is added to simulate infected blood. We have found that whole blood can be processed in our hollow devices without diluting the blood with diluents such as PBS or other isotonic additives. We have also found that adding a small volume of PBS to the blood increases the amount of plasma that is recovered, possibly by changing the viscosity. In some embodiments of the method, the volume of recovered plasma in which the bacteria are suspended makes no difference to the envisioned subsequent concentration of the bacteria for analysis. In other embodiments of the method, it is desirable to minimize the total volume so there is less waste and fluid handling after the plasma is recovered. While any volume of diluent can be added, in our experience it is more preferable to add from 0 to 8 mL of diluent per each 10 mL of blood, as this precludes the necessity of more powerful motors to rotate larger hollow devices.

Other additives that can be added to the blood before it is placed on into the hollow device include additional anticoagulants, wetting agents, platelet aggregants, cell aggregants, platelet disrupters or cell disrupters. Wetting agents are defined as chemicals that cause a fluid to have a smaller contact angle with the solid surface in contact with the fluid. Wetting agents are useful is causing the plasma to wet the surface of the hollow device and flow over the weir more uniformly, as will be described later. Platelet and cell aggregants cause platelets and cells to stick to each other, thus forming larger masses and producing faster sedimentation velocities as indicated by Equation 1. A common platelet aggregant is adenosine diphosphate (ADP). Cell aggregants can be antibodies or lectins that cause red cells to attach to each other. Other platelet or cell aggregants and their uses are known to those skilled in the art of hematology. Platelet and cell disrupters are chemicals that perforate, lyse, dissolve or otherwise disrupt the membranes of platelets and cells. They may be useful if the recovered plasma is to be subsequently filtered, and large amounts of whole platelets and whole blood cells might clog the filters. White blood cell disrupters should not be used if contamination by human DNA would interfere with bacterial analyses.

Placing the Blood in the Hollow Device

Blood can be placed into the hollow device by any number of methods, including pouring from a container or pipetting blood from the container into the hollow device. It is preferable to pipette the blood to deliver an accurate volume of blood into the hollow device. Placing more blood than the device is designed for will create more red cells in the recovered plasma. Placing less blood than the device is designed for will decrease the amount of plasma flowing down and decrease the total amount of bacteria recovered for analysis.

The lid may be open in the center for ease of pouring or pipetting blood into the device, or it may be closed or closeable so that after loading, no blood splashes out. If the lid is permanently closed then blood can be placed into the hollow device through a port in the lid, wall or floor. An open lid allows the separated plasma to be removed by pipette or aspirator or other suction device.

Other reagents can be added to the hollow device before or after the blood is added to the hollow device. These may be anticoagulants, diluents, wetting agents, platelet aggregants, cell aggregants, platelet disrupters, or cell disrupters.

Description of the Disk and Various Types of Disk Designs and Features

Many different embodiments of hollow devices can be employed in our method of separating bacteria from a blood sample. Some of these embodiments are described explicitly below. These descriptions are not to be limiting in any way. A person skilled in design can envision and produce embodiments of hollow disk and of methods that fall within the claims of this patent.

One of the most important design aspects of any embodiment is the size of the hollow device and volume of the vestibule. The shape and volume of the vestibule are designed to spread the volume of blood into a thick film over a designated surface area, such that the thickness of the blood layer is between 0.2 and 10 mm, and the distance that cells sediment is the same or less than the thickness of this blood layer. This thickness provides for a short sedimentation time when the hollow device is rapidly spun. A more preferred design creates a film thickness between 0.5 and 5 mm; a most preferred design creates blood film thicknesses between 1 and 3 mm, because in such a design the spinning time is short and the plasma layer is sufficiently thick that it can be easily separated. The resulting plasma is called "separated plasma". Separated plasma is distinguished from "clarified plasma", in that clarified plasma is free from blood cells, and the separated plasma layer in the methods described herein may still contain some cells. Thus separated plasma is usually considered to be partially clarified; in some cases of extended rotation time, the plasma layer may be fully clarified of RBCs. Once the separated plasma has migrated away from the separated cells, it is also called "recovered plasma", as this is the separated plasma that can be recovered and used in subsequent procedures.

Figure 2:
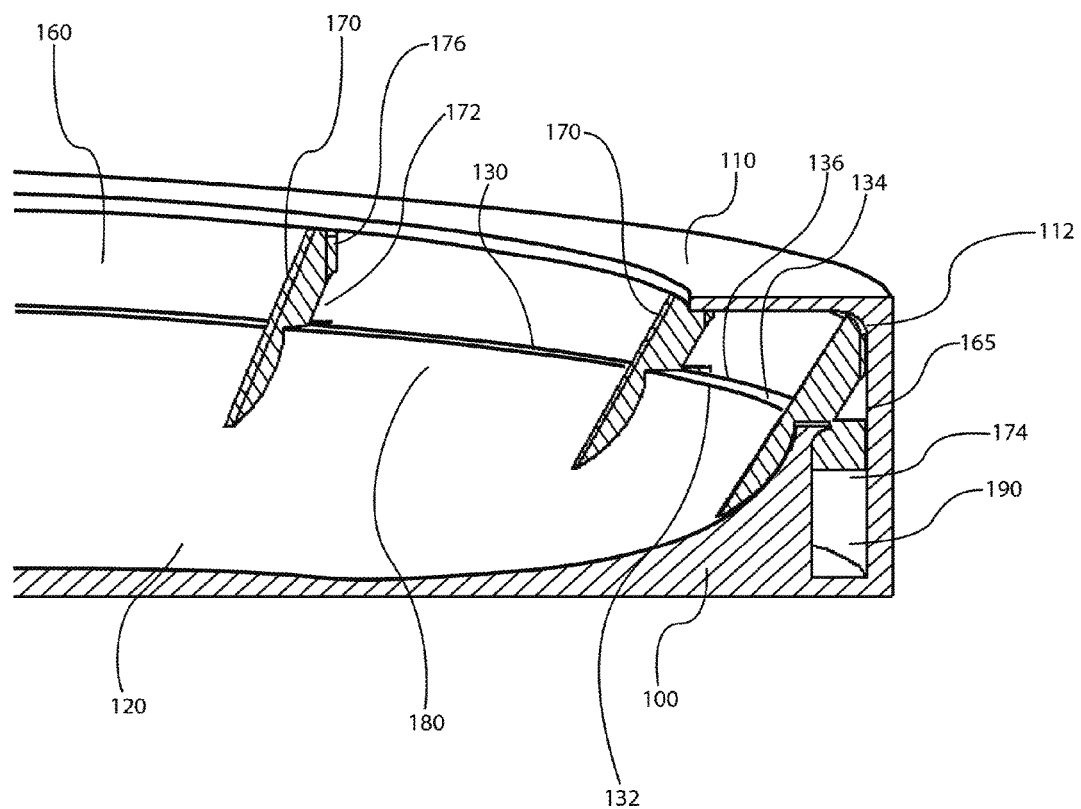
FIG. 2 depicts an illustration of the detail of the embodiment of the hollow device [100] illustrated in FIG. 1. In this illustration the connection of the bowl [120] with the weir [130] forms a nearly vertical slope [180]. The inward edge of the weir [132] has a square corner, and the outward edge of the weir [136] protrudes over the trough [190]. The top of the weir [134] is horizontal. There is a round fillet [112] in the corner formed by the partially open lid [110] and the back wall of the vestibule [165]. Triangular baffles [170] extend from the back wall of the vestibule to the slope of the bowl. Each baffle has a triangular window [172] in the upper portion of the vestibule [160] and a rectangular window [174] in the trough [190] region of the vestibule. There are round fillets [176] at the corners of the baffle and the back wall [165] of the vestibule, and not shown are similar fillets at the corners of the baffle and the partially open lid.
Figure 3:
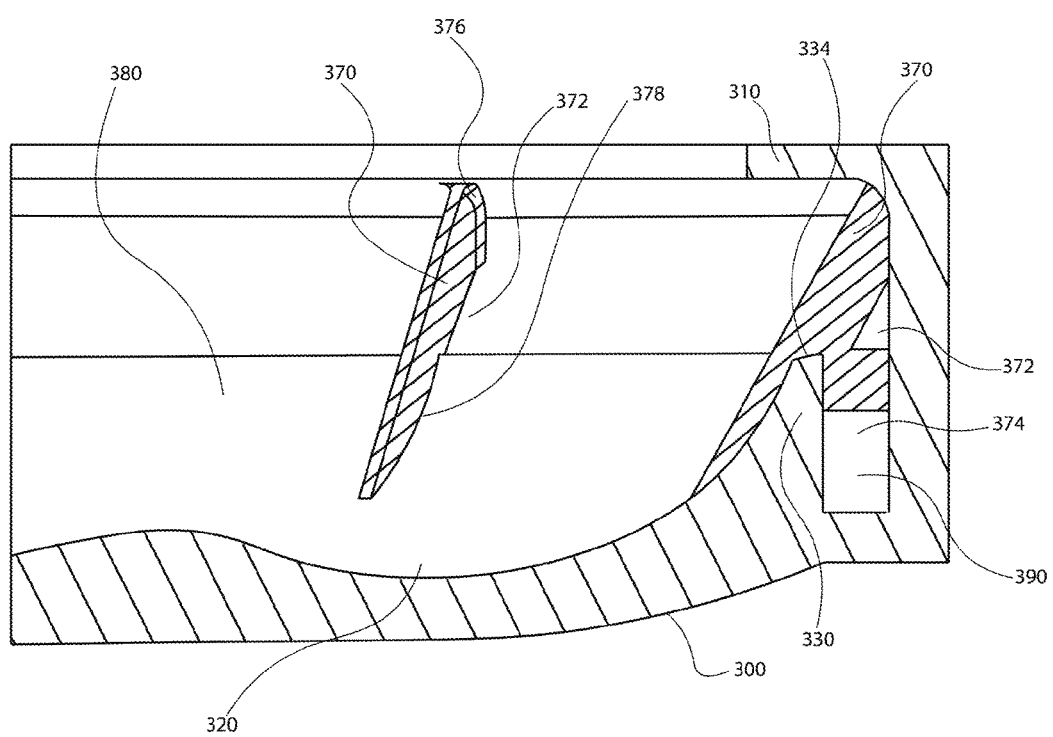
FIG. 3 depicts an illustration of a view of a certain embodiment of a hollow device [300] used in the method of this invention, which embodiment has a different style of weir [330]. The view is sliced through the middle of a triangular baffle [370] to show the profile of the baffle and weir. The top of the weir [334] is not horizontal, but is slanted inward toward the slope [380]. The baffles have fillets [376] and triangular windows [372] in the upper vestibule, and rectangular windows [374] in the trough [390]. There is no fillet on the baffle [378] where the baffle intersects with the slope [380]. Also shown are the bowl [320] and the partially open lid [310].
Figure 10D:
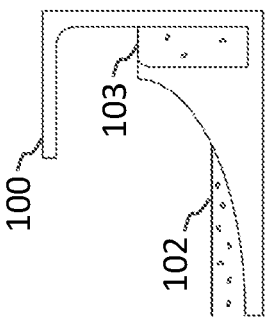
Figure 10C:
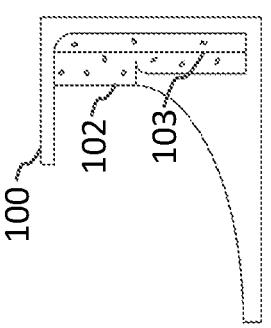
Figure 10B:
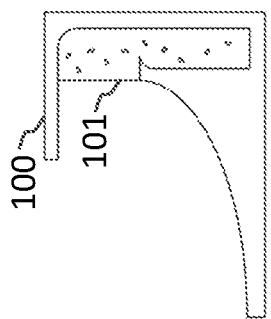
Figure 10A:
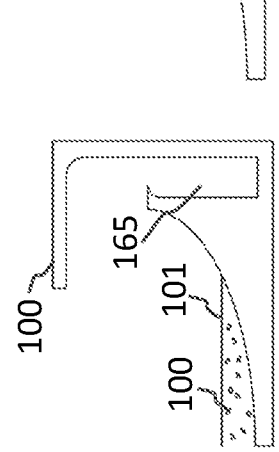
Figure 11D:
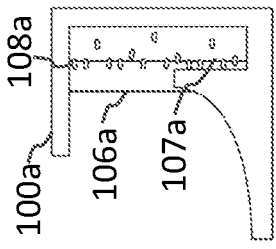
Figure 11C:
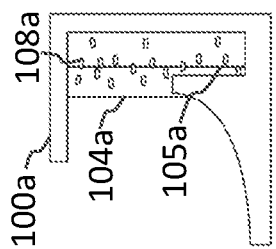
Figure 11B:
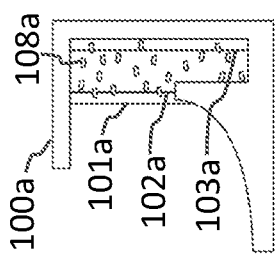
Figure 11A:
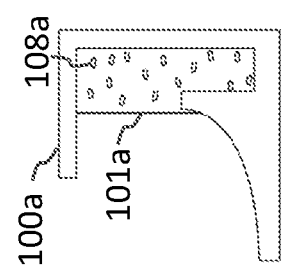

Our lab has separated *E. coli* and *Enterobacter cloacae* (*E. cloacae*) bacteria from fresh whole human blood using spinning hollow disk devices that are the designs shown in FIGS. 1-9 and variations thereof. Many embodiments of 12-cm-diameter hollow disks and some 8-cm-diameter hollow disks have been constructed from photopolymerizable monomers or an extruded thermoplastic, both using rapid-prototyping technology. Reference to these sizes is in no way limiting, as a range of sizes could be used in the method. In some simple embodiments the hollow device clips onto a CD spinner taken from a CD player. In most of our embodiments the hollow devices have vestibules with volumes of 7.0 mL or 8.5 mL, as blood is often collected in clinics or hospitals in 8 mL or 10 mL tubes. Of course, more or less blood might be used, which would require design and production of a differently shaped vestibule. Referring to FIG. 2, the lower portion of the vestibule is called the trough [190]. In many embodiments the volume of the trough is about one-half of the volume of the whole blood that is placed in the hollow device. The upper surface of the vestibule [160] is formed by the lid [110] placed at a height such that the volume of the vestibule is from 2 to 40 mL, more preferably from 4 to 30 mL, and most preferably from 7 to 20 mL. It is not necessary that the blood film thickness in the trough be equal to the film thickness in the upper portion of the vestibule. In most embodiments of hollow disks that we have constructed and in designing the volume of blood to be used, the blood thickness in the upper vestibule is equal to or thicker than the thickness in the trough. In most embodiments the lid extends radially inward beyond that required to form the vestibule and is most often open in the center for ease of placing blood in the hollow device or removing recovered plasma from the device. The lower surface of the hollow device inward from the vestibule is slanted toward the center of the disk; it is called the bowl [120]. Blood is usually pipetted into the cavity of the bowl of the hollow disk [100] through the partly open lid, as shown in FIG. 10a. When spinning starts, the blood [101] is flung into the vestibule, as shown in FIG. 10b. Within seconds sedimentation of WBCs and RBCs toward the outward wall of the vestibule [165] creates a clear amber-colored layer of plasma [102] on the inward edge of the fluid in the vestibule that grows in thickness as spinning time progresses. This is shown in FIG. 10c. The visual growth of this clear plasma layer eventually stops. After a pre-determined time, the disk is slowly decelerated to prevent remixing at the interface between the plasma and the cell-pack [103]. Finally at very low speeds, gravity causes the cell-pack to slide down the back wall of the vestibule [165] where it is trapped in a trough [190], while the plasma spills over the front edge of the weir [132] and flows into the bowl where it is collected with a pipette or vacuum aspirator. This is shown in FIG. 10d. FIGS. 11a, 11b, 11c, and 11d illustrate the layers that form based on density according to principles described herein, FIG. 11a illustrates a single layer of blood 101a in hollow disk 100a. FIG. 11b illustrates 3 layers with 101a layer having the least density, 102a layer comprising blood, and 103a layer having the most density, relative to each other. FIG. 11c illustrates 2 layers with 104a layer having the least density and 105a layer having the most density, relative to each other. FIG. 11d illustrates another variation of 2 layers with layer 106a having the least density and layer 107a having the most density, relative to each other. Distribution of cells 108a as shown serve as an indication of density.

The vestibule is the space at the periphery of the hollow spinning device into which the blood is flung. The trough is defined as the lower portion of the vestibule in which the red and white cells are expected to remain by gravitational trapping after the spinning is stopped. The trough is often the region of volume of the vestibule that resides below the top of the weir. The upper edge of the trough toward the center of the hollow device is called the weir; its purpose is to contain the cell-pack in the trough while allowing the plasma to flow out. The weir may be thin like a knife edge (<0.1 mm) or thick with thicknesses greater than 0.1 mm at the top edge; there are advantages to both thin and thick weirs. Thin weirs have better plasma flow-down, but they can chip during cleaning. A baffle [170] is a vertical ridge of material placed in the vestibule and sometimes extending inward into the hollow device beyond the inward edge of the weir. The drain [727] is a port or opening on the floor of the hollow device through which the blood can be inserted or the plasma withdrawn. The lid forms the uppermost surface of the vestibule; but is also extends further inward beyond the volume of the vestibule to prevent blood from splashing out.

We have developed numerous types of hollow disk devices, all of which have their advantages. The basic design in shown in FIGS. 1 and 2, which has a vestibule into which the blood is flung. The height of the vestibule can be varied to adjust the depth of blood in the radial direction. The depth of the blood layer, along with the spinning speed determines the time required to sediment the blood cells from the plasma. To process large volumes of blood, the device diameter can be large, the lid can be high, and the depth can be deep. When spinning at 3,000 rpm, it is preferred to have the depth of blood less than 5 mm to accomplish the separation in less than 5 minutes. More preferred is a blood depth in the radial direction of 2 mm or less as our results show that adequate separation with this design can occur with less than 1 minute of spinning.

Hollow spinning devices can be made of metal, ceramics, glass or plastics, using manufacturing principles known to those in the art. The advantage of hollow devices made of metal is that they can be autoclaved for sterilization, and they are durable if dropped. Manufacturing of intricate weir and baffle design is an advantage of some metals that can be formed by investment casting processes. Ceramic hollow devices can also be autoclaved; they can be made by casting or pressing or other methods known in the art of ceramic manufacturing. Glass hollow devices can also be autoclaved, and have the additional advantage that they are transparent for observation of the separation process and observation of the thoroughness of cleaning to remove residual cell-pack between uses.

Using plastics for hollow devices have the advantage of low cost, low density and ease of manufacturing. Large-scale manufacturing can be done by many means known to those in the art, including injection molding, casting, blow molding, and more. Prototype hollow devices can be made by the same processes or made by hand or made by rapid prototyping machines. The disks made in the research presented herein were initially made by hand and then made by two rapid prototyping instruments. One of our instruments lays down molten thermoplastic from a small traversing nozzle in the designated pattern. The other instrument uses a traversing photoactivating light to photopolymerized monomers released from a tiny nozzle, again in the designated pattern. Various materials were used with both rapid prototyping instruments, producing hollow devices of different surface wettability, different surface chemistry, and different light transparencies, including a clear plastic.

Composite materials can also be used. For example fibers or other fillers contained in a plastic matrix could be manufactured into hollow devices using techniques known in the art.

The purpose of the trough is to capture and hold the cell-pack as the spinning hollow device slows down and gravity pulls the denser cell-pack downward. The volume of the trough should be carefully designed to contain the estimated volume of the cell-pack. If the trough volume is too small for the cell-pack volume, cell-pack will streak into the plasma as the plasma drains, thus contaminating the sample with cells that could interfere with later processing of the plasma containing bacteria. As the normal hematocrit for males (39-50) is usually higher than for females (35-45), different trough volumes may be needed for blood obtained from men and women to separate bacteria most efficiently. Alternatively, the same trough volume could be used for both genders, but more blood would be pipetted into the hollow disk if the blood were from a woman than if the blood were from a man. Alternatively the same trough volume could be used for blood from both genders, and one would expect a slightly higher RBC concentration in the recovered plasma from a male; this may be an acceptable method if the subsequent processing of bacteria is not greatly affected by RBCs.

The trough can have straight or slanted sides, sharp corners or rounded corners, depending on the balance between manufacturing costs, "clean-ability" (if an expensive disk is to be cleaned and reused) and plasma clarity. Most preferred for good sedimentation is a trough with parallel vertical sides with a flat bottom; but this requirement can be relaxed for manufacturing and other needs, and for optimal recovery of bacteria and clean plasma. For example, we have discovered that if the inward (toward the center of the disk) wall of the trough is curve radially outward at the point it connects to the weir surface [136], there is less streaking of red cells pack into the recovered plasma. In this application the term "streaking" is differentiated from "remixing" as follows. Streaking is defined as when thin streaks of red-colored cell-pack have flowed over the weir with or into the plasma and yet there remains a distinct boundary between the plasma and streaks of cell-pack. In this patent application, "remixing" refers to mixing of the separated layers that occurs during deceleration, in which after the remixing occurs there is no distinct boundary between plasma and cell-pack and the color is intermediate between the amber color of plasma and the dark red color of cell-pack; in fact sometimes remixed blood has the same color as the fresh blood. Remixing is a phenomenon that may occur during deceleration; streaking is a phenomenon that may occur while the separated layer of plasma flows over the weir.

We have also discovered that the volume of the trough should be designed to accommodate the lesser consolidation of the cell-pack during shorter spinning times. For example, when blood is spun for only one minute, the volume of the cell-pack is larger than one-half of the blood volume and it slightly overflows the weir from a trough that is exactly one-half of the blood volume. However if the blood is spun for longer times, such as more than 2 minutes at 3,000 rpm, the cell-pack fits within a trough whose volume is one-half the volume of blood (excluding the volume of diluents added to the blood). We attribute this to loose packing of the cells during shorter spin times, leaving more plasma between cells in the cell-pack; whereas for longer spin times, more plasma is squeezed from the cell-pack forming a more dense pack that occupies less volume. Thus for shorter spin times the trough volume should be increased or the amount of blood should be decreased in order to reduce the amount of cell-pack streaking into the recovered plasma following spinning. Thus the trough volume should be carefully designed according to the spin time; we have found that as the spin time increases, the fraction of bacteria recovered in the plasma decreases, which is less desirable when the objective is to collect bacteria for subsequent analysis.

Description of Spinning Motor and Control Systems

While simple embodiments used a compact disk (CD) player to spin the hollow devices, any type of motor or other spinning device can be used to spin the hollow device. We have discovered characteristics of motors that reduce the amount of red blood cells in the recovered plasma. A motor that spins smoothly without any clicks or jerks in the rotation is essential to prevent remixing of the cell-pack with the plasma layer. The motor needs to be controllable down to zero rpm speed; those motors that slowed down but then stopped suddenly, instead of slowing all the way to zero rpm, produced remixing of cell-pack with plasma.

The examples contain details of three spinning systems that are useful in the practice of this method. In one system the spinning is actively controlled by hand by an operator using visual feedback from a tachometer. In another the spinning is programmed into and controlled by an Arduino. In the third system, the spinning is programmed into and controlled by computer software and an electronic feedback control system.

Spinning Speed and Time

We have spun disks between 10 and 5,000 rpm. Even higher spinning speeds are possible using other motor hardware known to those in the art. Higher spinning speeds are preferable because the time for separation decreases at higher spinning speeds. Most CD motors are designed to spin at 3,000 rpm, but we have electronically modified the CD motors to spin faster, and we have purchased other more powerful motors that can accelerate faster and run at higher angular velocities. Controllable motors are preferred so that the initial acceleration to the spinning speed and deceleration for drainage can be carefully controlled.

Equation 1 shows that the sedimentation velocity increases with the square of the angular velocity. Thus the sedimentation velocity is greatly increased and time required to carry out the separation is greatly reduced when the hollow device is rotated as quickly as possible and yet remain free of vibrations.

Symmetry around the central axis of rotation is needed to the extent that the disk does not wobble significantly when it spins. We have found a slight wobble to be tolerable, and slight wobble occurs sometimes because the rapid prototyping instrument does not print perfectly symmetrical devices. A large wobble of more than 0.5 mm (side-to-side) produces remixing during deceleration.

The multiplication product of the sedimentation velocity and the time of sedimentation is the distance that a particle travels. Thus time that the hollow device is rotated is a critical parameter. The time must be sufficiently long that most, if not all, of the fast-sedimenting particles have moved into the particle-pack. In the case of blood, the WBCs sediment faster than the RBCs, so their sedimentation is usually not the critical design parameter. To obtain plasma that is relatively cleared of RBCs, the minimum amount of sedimentation time for blood should be the time required for an average-sized RBC to move the distance from the inward surface of the vestibule to the edge of the cell-pack layer. The thickness of the cell-pack layer depends on hematocrit. Distributions in sedimentation velocity due to variations in size and density will require even longer times for the slowest RBCs to arrive. However, if the spinning time is too long, then bacteria continue to move to the surface of the cell pack and are precluded from recovery in the plasma. The if the multiplication product of bacteria sedimentation velocity and rotating time exceed the length of the clear plasma layer, all of the bacteria would be in the cell-pack and none would be recovered. Experiments may be required to obtain a balance between high bacterial recovery and good clearance of RBCs.

We also teach that some sedimentation occurs during acceleration and deceleration. Thus the total distance that a particle travels should be calculated from the time integral of all sedimentation velocities, including acceleration, holding at a constant speed, and deceleration.

Reducing Red Cell Concentration

We have built and tested many hollow device designs, of which each has various advantages. In most cases the parameters of interest were the quality of separation of blood cells (the clarity of the plasma), the amount of recovery of plasma, the practicality of implementing the design in a future commercial setting, and the fraction of bacteria that is recovered in the plasma. "Recovered plasma" refers to plasma that flows over the weir and is collected. In this specification, plasma refers to the clearer phase of the separated blood that has fewer RBCs, and does no imply that plasma in this context is totally free of RBCs. The plasma most often has been partly clarified of red cells. The "cell-pack" is the deep-red-colored phase that has a higher concentration of cells than found in the blood. There will always be some plasma retained between cells in the cell-pack. The cell-pack also contains white cells, platelets and some bacteria to differing amounts, depending on the speed and time allowed for sedimentation.

We have discovered that there is a trade-off between the reduction of red blood cells in the recovered plasma and the recovery of bacteria from the blood. As spinning time or spinning speed increase, there are fewer RBCs in the recovered plasma and there are fewer bacteria in the recovered plasma. Detailed examples are presented later. We hypothesize that with increased time, more of the RBCs are sedimented in the cell-pack. Table 1 shows that there is a distribution of RBC mass density, and so some RBCs will sediment more slowly and will generally enter the cell pack later. But during the time it takes to sediment all the RBCs, the bacteria are continually sedimenting toward the cell-pack, and fewer bacteria are found in the plasma. One processing scenario would be to experimentally or theoretically determine the spin time and deceleration time in which all RBCs arrive in the cell-pack, thus giving a cell-free recovered plasma. But this plasma would have fewer bacteria in it than if a few RBCs were tolerated and the spin time or spin speed were reduced. The optimum spinning conditions are determined by the tolerance of the subsequent analysis process to the presence of RBCs.

Adding Platelet Coagulants

We observed using a microscope that recovered plasma from blood collected in EDTA vacutainer tubes contained higher numbers of platelets than found in recovered plasma from blood collected in citrate or heparin tubes. Although platelets do not contain DNA, they may interfere with subsequent processes and may not be desirable, depending on the type of analysis. We discovered that by adding adenosine diphosphate (ADP) to formulate a concentration of around $1 \times 10^{-5}$ g ADP per mL in the EDTA-anticoagulated blood, there were fewer platelets observed in the recovered plasma. ADP has the ability to cause platelets to aggregate together, even when they are in blood that has been moderately anticoagulated. We believe that the platelets are aggregating together before and during the spinning, and the larger size of the platelet aggregate increases the sedimentation velocity so that they are sedimented more rapidly into the cell-pack. Adding ADP makes a large practical difference in any subsequent filtration process of the recovered plasma. For example, the plasma recovered from EDTA-treated human blood readily clogs a 0.45-μm polysulfone membrane filter [VWR International, Radnor, Pa.], while plasma from EDTA-treated blood that contained $1.22 \times 10^{-5}$ g ADP per mL can pass through a 0.45-μm polysulfone filter.

Maximizing Bacterial Recovery

Wettability.

Our research has shown that the wettability of the surface of the hollow device is critical, especially the wettability in the region of the weir. We have observed an important issue pertaining to wettability: at the conclusion of spinning, if the plasma does not wet the material surface, it does not flow down uniformly. There is plasma "hold-up" at the non-wetted boundary at the edge of the weir, and the separated plasma bulges outward over the non-wetted surface as gravity pulls it downward from the upper region of the vestibule. In non-wetting situations sometimes it takes many seconds after the spinning has stopped until the bulging plasma finally "breaks through" at some point; then much of the plasma in the upper section of the vestibule flows circumferentially around the upper part of the vestibule and down through the single point of breakthrough. Unfortunately this circumferential flow also entrains some of the cell-pack and the plasma flowing down (which we will call "flow-down") has streaks of red-colored cell-pack in it. We also hypothesize that some cell-pack from the trough immediately below the point of breakthrough is convected upward and over the weir, also contaminating the clarified plasma with streaks of cell-pack. Uniform flow-down around the entire circumference of the weir is most preferred for obtaining plasma free from streaks of cell-pack.

It is preferable to have an advancing contact angle less than 90° for the plasma on the material. It is more preferable to have an advancing contact angle less than 30°, and most preferable to have an advancing contact angle of less than 5°. There are various methods known in the art to decrease the contact angle, which corresponds to an improvement in the wettability of the material surface by the separated plasma. We have employed many techniques to increase the wettability of the plastic surfaces used in our hollow devices. Soaking in nitric acid, sulfuric acid and hydrogen peroxide increases the wettability and decreases the advancing contact angle; likewise exposure to other oxidizing chemicals known in the art will increase wettability. We have increased the wettability by processing the hollow device in a radiofrequency (RF) discharge chamber for 3 minutes with oxygen gas; likewise other RF or electric discharges in other gases known in the art will increase the wettability. Chemical vapor deposition of silicone dioxide or other wettable materials will reduce the water contact angle.

Amphiphilic polymers and molecules contain a hydrophobic region of interaction and a hydrophilic region of interaction. We have soaked the interior of the hollow device in a solution of amphiphilic block copolymer (Pluronic P105 and Pluronic F108) in which the hydrophobic portion of the block copolymer attaches to the hydrophobic plastic and the hydrophilic portion is free to interact with and wet the plasma so it has a lower contact angle. Likewise other amphiphilic block copolymers could be used. We have used small amphiphilic organic molecules also as wettability enhancers. Briefly exposing the surface to a solvent containing small amphiphilic organic molecules attaches the hydrophobic portion of the molecule to the plastic and leaves the hydrophilic portion on the surface to enhance wettability. We discovered that gamma-amino butyric acid is a wetting agent for the hollow devices that are made by the thermoplastic rapid prototyping instrument. The hollow devices made by the photopolymerization rapid prototyping instrument were less wettable with gamma-amino butyric acid, but a soak with sebacic acid in methanol provided some improved wettability, particularly when combined with proper weir design and baffle design. Other amphiphilic molecules and chemical treatments known in the art can be used likewise to increase wettability. When pre-treating the hollow devices by soaking with chemical solutions, the soaking solution is removed and the hollow disk is rinsed and dried before the blood is deposited in the hollow device.

Weir Design.

We have discovered that in cases in which the wettability is not perfect, particularly when the contact angle of plasma on the hollow device surface is greater than 5°, the uniform drainage of plasma, and avoidance of cell-pack entrainment, can be enhanced by proper weir design. We have employed thick uniformly high weirs, thin uniformly high weirs, and slotted weirs with success, all with various advantages. A slotted weir has the bottom of the slot placed level with the top of trough, and the top of the slot is at a higher level than the top of the trough. This increases the surface area of contact between plasma and "teeth" of the slotted weir and helps make a more uniform flow of plasma when spinning stops. A thin weir of uniform height has the advantage that the hollow device is less massive and that the plasma quickly drains down the steep slope when spinning stops; but if this hollow device is reused, the thin weir is sometimes nicked or broken during cleaning. A thick weir of uniform height is rarely nicked during cleaning, but there is a flat region on top of the weir, and if this surface is not wettable, the plasma does not flow down well. We have found that a combination of making the surface wettable and using a thick weir with a flat top provides more uniform plasma flow-down and minimal streaking with red-colored cell-pack. In some designs the upper surface of a thick weir is not horizontal, but may be sloped to promote flow of the plasma over the weir. We have also made designs in which the wall of the trough where it meets the weir is not vertical, but the wall of the upper section of the trough is curved radially inward or radially outward where it meets the top surface of the weir. We have discovered that when the upper section of the trough adjacent to the top of the weir is curved radially outward (curved into the trough volume) there is less streaking of RBCs in the recovered plasma.

Several examples of weir designs are shown in FIGS. 2-5, and FIGS. 7-8.

Slope Design.

The slope of the hollow device from the inward edge of the weir to the bowl affects the rate of plasma flowing down. Several examples of slopes are shown in FIGS. 2-5, and FIGS. 7-8. It is preferable for the slope to be steep so that gravity will cause the plasma to flow down quickly after spinning stops. We have found that when wetting agents are used to make the surface more wettable to the plasma, the slope does not need to be as steep to obtain plasma of sufficiently low streaking and low red cell counts that the plasma can be filtered on a 0.45 µm membrane filter. When wetting agents are not employed a steep or vertical slope is preferred. Most preferred is to have both a steep slope and some surface treatment to promote wettability.

Baffle Design.

The baffles serve at least two purposes. One function is to reduce the possibility of remixing of cell-pack and plasma during deceleration of the spinning hollow device. When the disk slows down, the more inward layer of separated plasma tends to slide in the circumferential direction across the more outward layer of denser cell-pack material. If this sliding is too large in magnitude, it may cause remixing at the interface between the plasma and cell-pack and introduces many cells into the plasma. We believe that in some cases remixing can be reduced by placing baffles in the vestibule, which baffles may reduce the circumferential sliding and possibility of remixing. Our visual observation is that with more baffles there are less red cells in the recovered plasma. However, if the hollow devices need to be cleaned and reused, having a high number of baffles makes cleaning much more time consuming. We have found that 8 to 20 baffles is a good balance when cleaning is needed, and even more baffles could be used if the hollow devices are used only once and then discarded.

The baffles may be of uniform thickness with a rectangular shape having a vertical inward edge or of uniform thickness with a triangular shape with a slanted inward edge (see FIG. 2, [170]), or be of non-uniform thickness (see FIG. 5, [571]) or other shape that will become apparent to those skilled in mechanical design. Baffles can be solid or can have passageways through them, made by cutting out "windows" through the baffles. Windows in the trough region of the baffle (see FIG. 2, [174]) allow easier removal of cell-pack if the hollow device is to be reused. Windows in the upper region of the vestibule (see FIG. 2, [172]) allow plasma to flow circumferentially in case there is not uniform flow-down over the edge of the weir; the windows allows the plasma to flow circumferentially to the point of flow-down, and minimize the entrainment of cell-pack into the plasma from the trough. Triangular baffles provide the same benefit as an upper window because plasma can pass in front of the baffle if there is non-uniform flow-down. Windows can be square, triangular, circular or any other shape. Windows or triangular slanting baffles are preferred in the upper part of the vestibule when the wetting of plasma on the weir is poor and there is a possibility of non-uniform flow-down following spinning; the high flow of plasma breaking through in one point tends to convectively drag cell-pack up and over the weir if the plasma above the cell-pack cannot flow circumferentially due to solid vertical baffles that block the flow. By using slanted baffles and upper windows, the plasma can flow circumferentially through the windows or in front of the baffle and down over the weir where the break-through is located. Fewer streaks of red-colored cell-pack are observed in the recovered plasma when using spinning devices with baffles having upper windows.

We have discovered a second very important purpose of baffles. When baffles extend past the weir (see FIG. 2, [170]), they provide a wetted surface that starts the downward flow of plasma over the edge of the weir. The flow over the weir is initiated in the corners made by the baffle intersecting the edge of the weir. We have observed that having more baffles extending beyond the weir produces more uniform flow-down and less streaking of cell-pack into the recovered plasma. However, more than 50 baffles in a reusable device would make cleaning very time consuming. Most preferable is a balance between more uniform flow-down and cleaning time, which we have found to be 8 to 20 baffles. More baffles could be preferable if automated cleaning methods are available, or if the hollow device are designed for a single use. As mentioned before, the contamination of plasma with the RBCs does not reduce the number of bacteria recovered, but in some cases it may make any subsequent identification of the bacteria more difficult, depending on the subsequent analytical technique; and thus it is more desirable to have a minimal amount of cell-pack flowing over the weir after spinning stops.

We have discovered that on some materials, the plasma has a small receding contact angle of <30°, which can be used advantageously to initiate draining over the weir and promote uniform flow-down. When the inward edge of the weir is vertical, the initial slope for the plasma to flow down is vertical. In the case of a small receding contact angle and a vertical slope, we have discovered that if the vestibule volume is adjusted such that during spinning the vertical or nearly vertical slope is wetted with a thin layer of blood, then when spinning is completed, the plasma has already wetted the vertical slope and the plasma starts flowing down immediately and fairly uniformly around the circumference of the wetted vertical slope. The thickness of the blood covering the slope need only be from 50 to 500 µm. It is less advantageous to have a blood thickness greater than 0.5 mm on the vertical slope because a layer of cell-pack forms on the surface of the vertical slope, which may slide down and contaminate the plasma with streaks of red-colored cell-pack. However, when the blood thickness is 100 µm or less the RBCs appear to be pressed firmly against the vertical slope and they rarely flow down with the plasma.

Although a small receding contact angle is advantageous for initiating more uniform plasma flow-down, the small receding contact angle promotes the retention of plasma in the corners of the upper volume of the vestibule. Some plasma remains in the corners of the upper vestibule and is difficult to collect because it does not drain. We have discovered that the solution to this problem is to avoid all sharp corners in the upper part of the vestibule. We have found that when we put a fillet on interior corners of the upper portion of the vestibule, the plasma drains more readily and more volume of plasma is recovered. Typical places for filleted corners are the corner between the back wall and lid of the upper vestibule, and the corners between the baffles and the back wall and lid. Preferred fillet radii are between 0.2 and 2.0 mm. Fillets of larger radius unnecessarily occupy volume that could be used for blood, and fillets of less than 0.25 mm radius do not appear to promote plasma drainage as well. Some fillets are shown in FIG. 2, items [176] and [112]. Fillets in the lower corners of the trough do not promote plasma drainage, but they do enable easier cleaning of the cell-pack if the hollow device is to be reused. Fillets on any portion of the baffle extending beyond the weir are avoided because these sharp corners (of non-filleted joints) promote wetting of the dry surface by the plasma, which then more readily flows down these corners after the spinning has stopped.

With the weir and baffle design described above, the plasma starts creeping over the edge of the weir just before the hollow device stops rotating, even without the addition of wetting agents or surface treatment of the plastic device. Once the device stops, more flow is observed. The time to complete the migration of plasma over the weir into the bowl of the device is on the order of 10 seconds, and pipetting typically can start about 15 seconds after cessation of spinning. The time to complete the migration of plasma can be reduced by adding surface treatments or wetting agents, as known by those skilled in the art of surface science.

Slowing the Hollow Device to Avoid Instability

We discovered that the rate of decelerating the spinning disk has a large impact on the clarity of the recovered plasma. If the disk is decelerated to quickly, there is a remixing of the red-colored cell-pack with the plasma layer even before the spinning stops completely, which remixing greatly increases the number of cells in the recovered plasma. This remixing phenomenon is very different than streaking of cell-pack into the plasma as plasma flows down from the weir. When using transparent plastic hollow disks, the separated layers of plasma and cell-pack are easy to observe in the vestibule. During deceleration they remain separate until suddenly, in less than 1 second, the layers mix and separation is no longer visible. This occurs while the device is still spinning. The fluid that flows down appears to be the same color as the original blood.

To investigate why remixing occurs we used a high-speed camera (model v1610, Vision Research, Wayne, N.J.) operating at 10,000 frames per second to record the transition from separated to mixed layers as the hollow disk is decelerating. Our observations are that the transition is initiated by a fluctuation in the smooth interface between the plasma and cell-pack layers, or sometimes by a wisp of red color winding into the plasma layer. This bend in smooth interface between layers or wisp of red quickly grows and spreads red color into the plasma layer. In less than a second the red color spreads into where amber-colored plasma had been. These observations are reminiscent of Kelvin-Helmholtz instabilities that grow at the interface of layers of fluid in which the fluids are layered because of their density (A. P. Hooper and W. G. C. Boyd (1983) "Shear-flow instability at the interface between two viscous fluids," *J. Fluid Mech.*, 128, 507-528). Kelvin-Helmholtz instabilities are initiated when the shear stress at the interface exceeds a critical value; then mixing at the interface is initiated and grows. Kelvin-Helmholtz instabilities are known to those in the art of fluid mechanics.

This discovery that recovery of clear amber-colored plasma containing bacteria is highly sensitive to the rate of decelerating the hollow device is a non-obvious aspect of the method of this invention, and is so critical to the success of the method. At high rotational speeds, the interface between plasma and cell-pack is very stable because the centrifugal force keeps the denser cell-pack from penetrating into the plasma layer, even when there are high shear stresses caused by rapid deceleration. However, as the device decelerates and as its absolute angular velocity decreases, the stabilization from centrifugal force decreases to the extent that at some value of slow angular velocities, the shear forces at the interface become larger than the centrifugal stabilization forces, and remixing occurs at the interface. Thus the device can be decelerated rapidly when at high rotational speed, but must be decelerated more slowly at low rotational speed, in order to keep the interface stable.

We have found that for 12-cm-diameter disk-shaped hollow devices similar to those shown in FIG. 1, the disk can be accelerated to 3,000 rpm in 22 seconds. Stable layers of plasma and cell-pack form during the next 38 seconds. Then the device can be rapidly decelerated from 3000 rpm to 285 rpm over 76 seconds and no remixing occurs. The layers of separated plasma and cell-pack will not mix when the device is subsequently decelerated at a rate of less than 1.18 rpm/sec when the angular speed is less than 285 rpm. Hollow devices of different geometries will require different deceleration rates to avoid remixing, and some experimentation will be required to find the best deceleration rate to avoid remixing and yet complete the separation and flow-down of bacteria-laden plasma in a reasonably short time.

Figure 9:
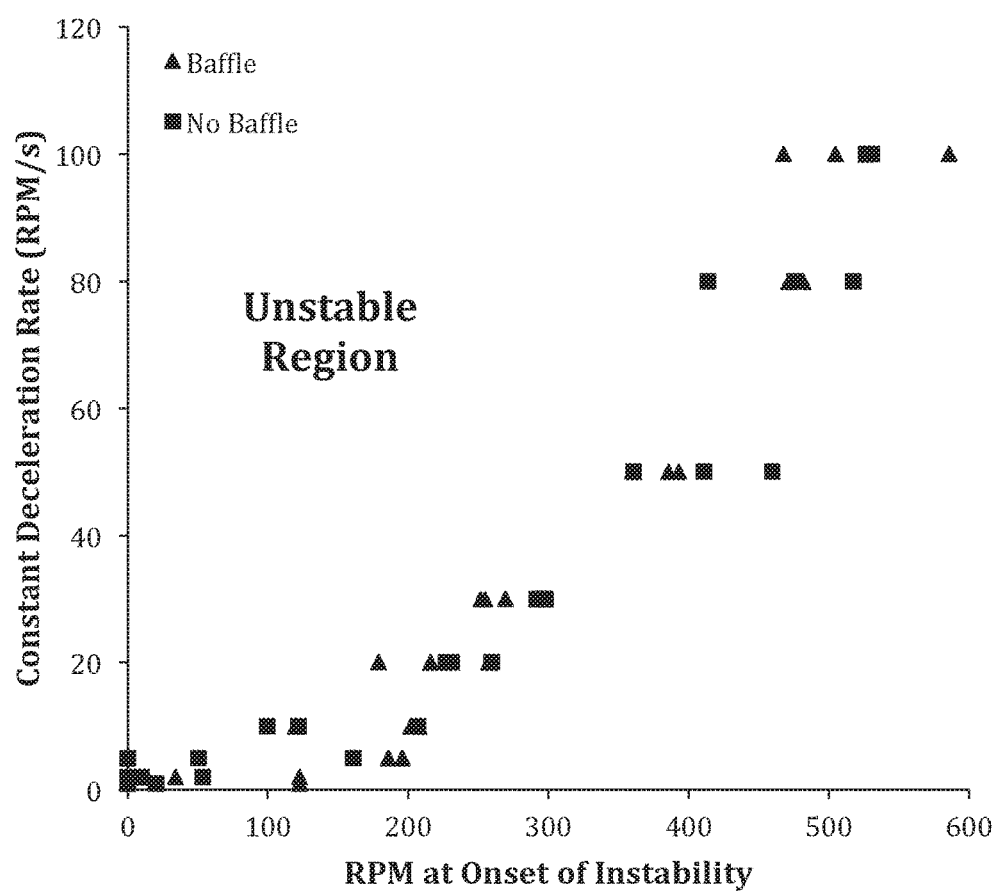
FIG. 9 presents graphical data measured in an embodiment of a hollow device used in the method of this invention. Experiments were done with 7.0 mL of blood and 1.5 mL of PBS in a 12-cm-diameter disk-shaped hollow device similar to that illustrated in FIG. 1 and a similar device without baffles. After sufficient rotation to form a plasma layer and a cell-pack layer, the hollow device was decelerated at a constant deceleration rate, given on the ordinate of the plot. When the interface between the plasma layer and the cell-pack layer became unstable and remixing occurred, the rate of rotation (measured in rpm) was recorded and is given by the value on the abscissa. To the left side of the locus of data points is the unstable region. To the right side of the locus of data points is the region of stability in which remixing does not occur.

Example 13 and FIG. 9 give experimental results of when the deceleration produces instability at the interface, resulting in remixing.

Removing the Recovered Plasma

While the hollow device is carefully and slowly brought to a complete stop, the more dense layer of cell-pack is pulled down by gravity to fill the region of the trough. The less dense layer of plasma remains above the more dense cell pack, and gravity also pulls it down, but pulls it over the weir. The hollow devices are designed so that gravity will pull down the plasma layer, causing the plasma to migrate to a low place in the bowl of the hollow device. Gravity drives this migration of plasma to a low region of the hollow device and gravity produces the migration of cell-pack into the trough. In at least one embodiment the method of this invention, separation of plasma and cell-pack is accomplished by gravity-driven means instead of by pumps or skimming or other mechanical methods.

Once the plasma has migrated to a low place, the plasma can be removed by pipetting it from the device. Alternatively it can by collected by aspiration or other vacuum-assisted methods to remove the plasma from the hollow device. Another embodiment of the method of removal is to place a port at the low place in the bowl to which the plasma migrates. The port is closed during placement of blood and spinning and plasma migration, but then is opened to allow to plasma to drain from the device. Alternatively the hollow device can be pressurized, which pressurization both opens the port and pushes out the recovered plasma through the port.

Once the bacteria-laden plasma has been recovered, it can be transferred to other operations and methods that concentrate the bacteria in preparation for analysis. We have already mentioned filtration through a porous membrane filter. Other methods used to concentrate the bacteria include ultrafiltration, centrifugation, size exclusion chromatography, physical capture in porous media, chemical capture in porous media, physical capture on magnetic beads, physical capture on non-magnetic beads, chemical capture on magnetic beads, chemical capture on non-magnetic beads, physical capture on bubbles, and chemical capture on bubbles. Ultrafiltration employs a membrane with no pores or with nanoscopic (sub-micron) pores in which high pressure difference pushes some fluid through the membrane, leaving behind the bacteria and concentrating it. Conventional centrifugation in a test tube can be employed to form a pellet of bacteria at the end of the tube. In size-exclusion chromatography, large particles such as bacteria quickly pass through the porous media in a packed column, while the small molecules and fluid in general pass more slowly. Capture in porous media includes the process of flowing the recovered plasma through a column or bed of solid or semi-solid particles that have affinity for the bacteria such that the bacteria attaches to the porous material and can be eluted later from the material. Capture on magnetic beads or particles is useful because the magnetic beads with attached bacteria can be collected from the suspension and transferred out of the plasma. Non-magnetic beads that capture bacteria could be separated from the plasma by physical methods such as filtration or centrifugation. Bubbles that capture bacteria can be separated from the plasma by floatation or centrifugation. These methods are known to those skilled in the arts of separation technologies. For clarity, we will define the primary distinguishing difference between physical capture and chemical capture: chemical capture involves the formation of chemical bonds, including hydrogen or ionic bonds, between a bacterium and a solid, liquid or gas substrate; physical capture involves mechanical entrapment and non-chemical-specific surface interactions, including hydrophobic association of the bacteria with a hydrophobic surface.

Metered Volume in the Vestibule

As it is preferred to recover the maximum amount of bacteria while retaining the cell-pack in the trough, the volume of the trough and vestibule must be carefully designed to adequately trap the cell-pack. If the cell-pack is larger than the trough volume, streaks of cell-pack will contaminate the clear plasma. If the medical technician places the proper amount of blood in the hollow device, placement of oversized volumes is precluded. However, if by accident the medical technician places too much blood in the hollow device, the plasma and cell-pack may still separate, but during flow-down the trough will overflow with red-colored cell-pack and the recovered plasma will become contaminated. This unfortunate situation can be avoided by designing an overflow safety feature into the design of the hollow device. There are several designs of such an overflow safety feature, known to those in the art of fluidic design. We have designed more than one embodiment of overflow safety for disk-shaped hollow devices that are not intended to be limiting in any way, but are intended to teach this principle.

Figure 4:
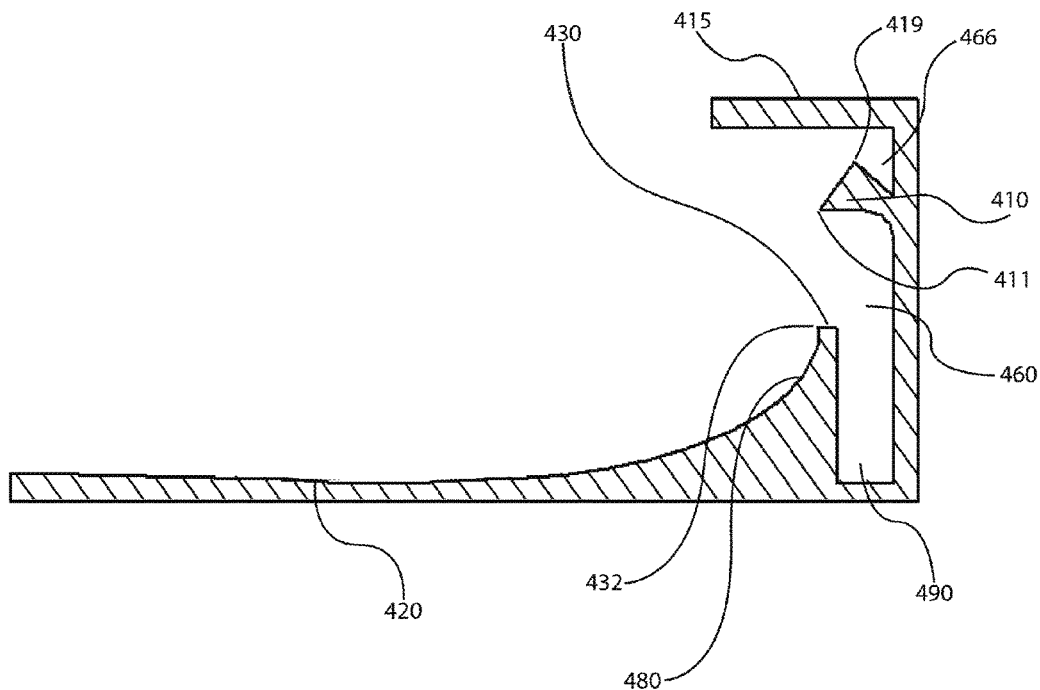
FIG. 4 depicts an illustration of the detail of a cross section of a certain embodiment of a hollow device used in the method of this invention. This embodiment illustrates a metered blood vestibule [460] in which excess blood will immediately overflow to an overflow chamber [466] and not contribute to plasma or cell-pack. The volume of the metered vestibule is defined by the extension of the partially open primary lid [410] positioned over the weir [430]. In this embodiment the inward edge of the primary lid [411] is exactly over the inward edge of the weir [432]. A partially open upper lid [415] prevents overflowing blood from escaping during rotation. When rotation stops a retaining weir [419] in the primary lid [410] prevents escape of blood from the overflow chamber. This embodiment illustrates a rectangular trough [490], a steep slope [480] and a bowl [420].

A first embodiment of a metered hollow device is one that has two "lids" and two types of compartments on the periphery of the hollow device, as shown in FIG. 4. The innermost (or lowermost) vestibule (FIG. 4, [460]) forms the thick film of blood as specified previously. It is called the "blood vestibule". Its volume is controlled by forming the primary lid (FIG. 4, [410]) of this vestibule to have a very specific inward radial length so that the inward edge of the lid will create the desired thickness of blood. If by accident too much blood is placed in the hollow device, when rotation begins the excess blood will overflow this primary lid and flow outward and upward to be collected in another compartment called the overflow chamber (FIG. 4, [466]). This could be on top of the blood vestibule or outward (in the radial direction) beyond the primary vestibule. The volume of this overflow chamber is defined by the upper lid (FIG. 4, [415]) and a retaining weir (FIG. 4, [419]). The upper lid protects the clinical technician from splashes of contaminated human blood. This overflow chamber may also have a weir (FIG. 4, [419]) or a trough or other design element known to those in the art that will prevent the blood in the overflow chamber from flowing to the bowl of the hollow device when spinning stops.

Figure 5A:
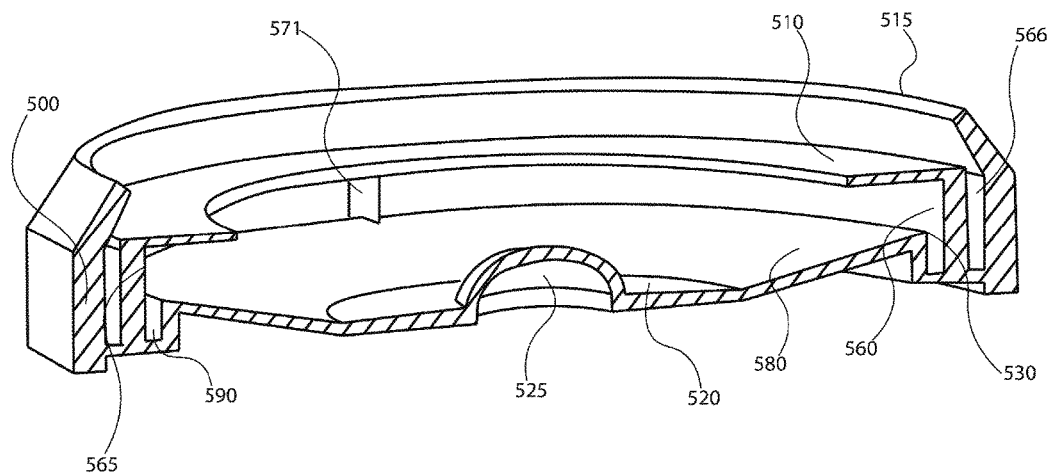
FIGS. 5A and 5B depict an illustration of a certain embodiment of a hollow device [500] used in the method of this invention. This illustration shows a different embodiment of a metered blood vestibule [560] in which excess blood will immediately overflow to an overflow chamber [566] and not contribute to plasma or cell pack.
Figure 5B:
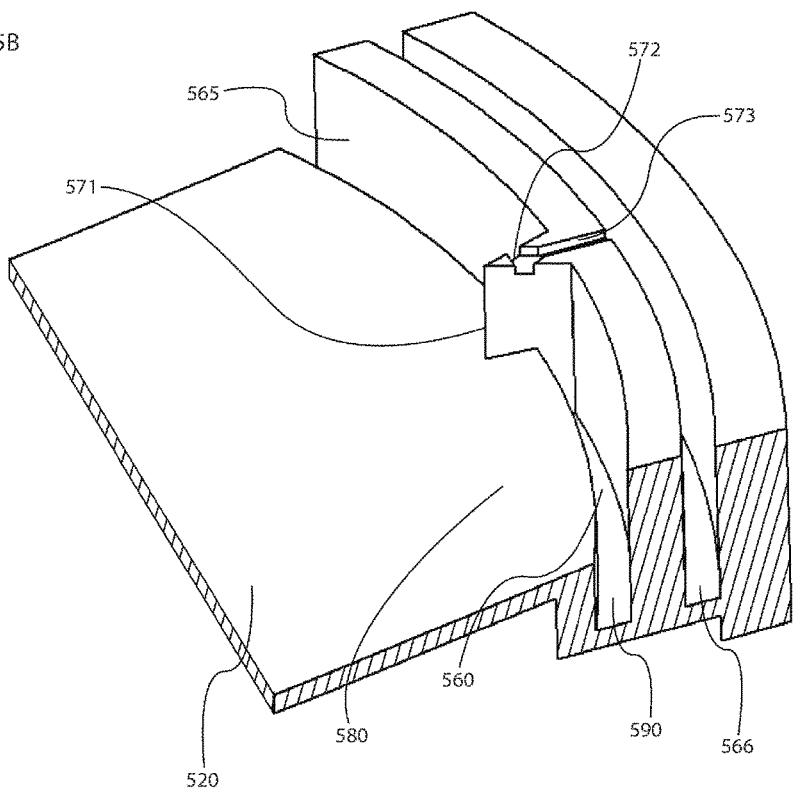

A second embodiment of an overflow safety feature that works well for a hollow device is illustrated in FIGS. 5A and 5B. For clarity the two lids (FIG. 5, [510] and [515]) of this hollow device are not shown in FIG. 5B. Although any number of baffles could be used, the embodiment shown in FIG. 5 uses two wedge-shaped vertical baffles [571], shown from different angles in 5A and 5B. This design places the overflow chamber [566] further outward of the blood vestibule [560] used to separate plasma from cell-pack. The only entry into the overflow chamber is through a small overflow drain (FIG. 5, [573]) near the top of the wedge-shaped baffle. This drain could have a rectangular or circular cross section with preferable width or height dimension, for example, of 200 to 1,000 micrometers. The entry into the drain (FIG. 5, [572]) is placed at the top near the primary lid (FIG. 5, [510]) and also at a radial position corresponding to the radial position of the desired thickness of the thick film of blood in the blood vestibule. If more blood is placed into the device than the specified design volume, then upon commencement of rotation the blood is flung into the blood vestibule and the excess blood enters the drain and is quickly pushed down the drain by centrifugal force into the overflow chamber. Only the specifically designed thickness of blood remains in the blood vestibule, and as gravity pulls the cell-pack into the trough (FIG. 5, [590]) at the end of spinning, the cell-pack does not overflow the trough. The entry into the drain could be placed at any height above the top of the weir, and it is more preferred to have the entry to the drain at a high position near the lid so that upon commencement of rotation of a proper volume of blood, accidental entry of blood into the drain is reduced or avoided. Accidental entry of blood is avoided even more by splitting the entry to the drain into two entrances (FIG. 5, [572]) whose openings are nearly perpendicular to the radial direction, as shown in FIG. 5B.

Other Shapes of Hollow Devices

Figure 6:
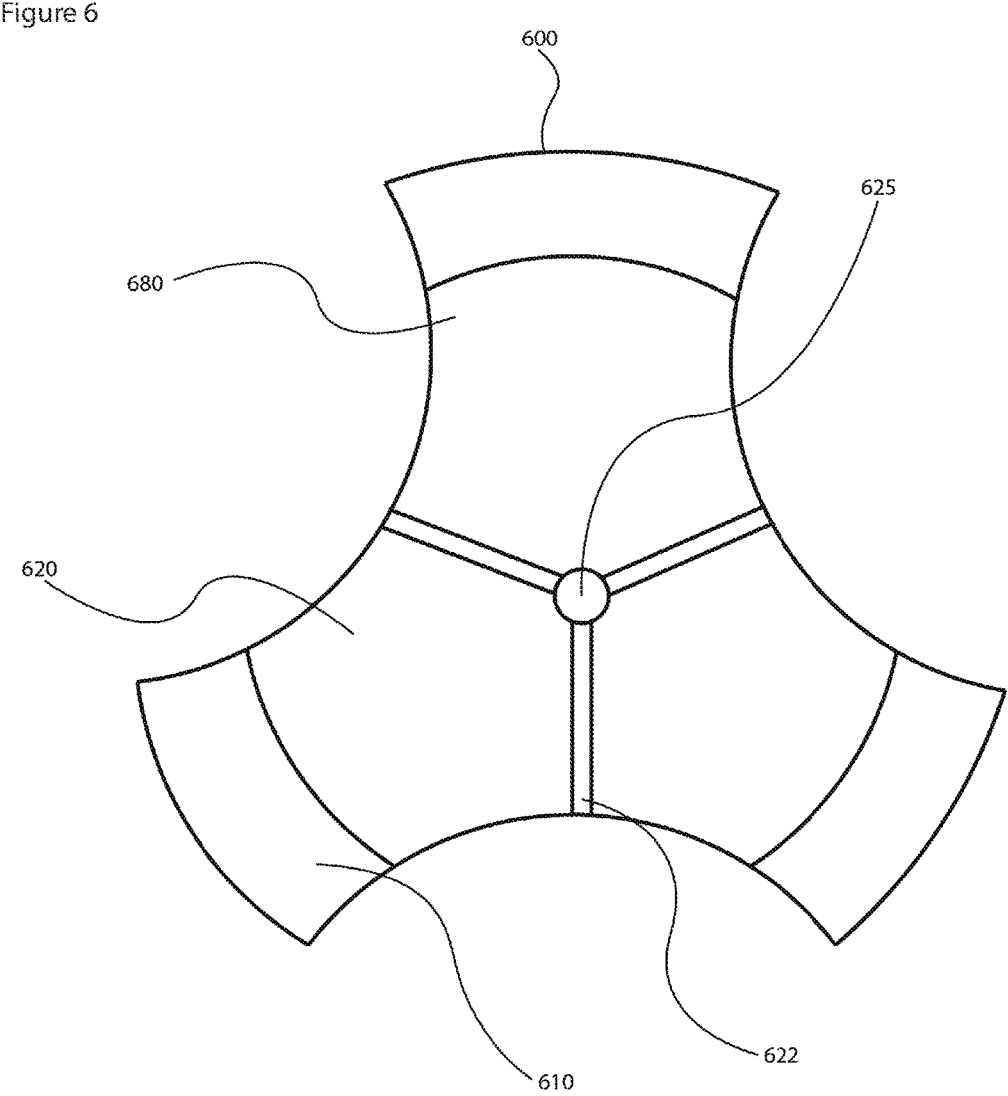
FIG. 6 depicts an illustration of an embodiment of a non-circular hollow device used in the method of this invention. The figure illustrates a three-lobed hollow device [600] that is balanced around its axis of rotation. There is also shown a partially open lid [610], a bowl [620], a slope [680], and a connection to the rotating spindle [625]. There are barriers [622] that separate the different sections of the bowl.

Discontinuous hollow devices. We have manufactured and used many embodiments of hollow devices that are circularly symmetric around the axis of rotation. However, one skilled in the art will recognize that the hollow device need not be circularly symmetric to accomplish the desired separation. Embodiments of the hollow device that are noncircular hollow devices with two, three or more lobes and that are balanced around the axis of rotation could also be used, such as illustrated in FIG. 6. The advantage of such devices are that the baffles are replaced by walls that provide the damping of circumferential flow at the end of spinning, and that provide the wetting of the plasma over the weir and down the slope as described previously. Another advantage is that more than one sample may be processed at once by placing each sample in a separate lobe of the hollow device.

Spinning Spherical Devices.

In addition to using hollow disks described above, we have executed embodiments of this method that employ a spinning sphere with an opening at the upper pole of the sphere and a vestibule at the equator. This shape can also be blow-molded or otherwise easily made in one part by techniques known in the art of plastic manufacturing. The cell-pack collects in the vestibule and the plasma easily drains down when spinning stops and can be collected by a pipette through the hole at the top or through a drain at the bottom. However, there is some streaking with this design.

Figure 7:
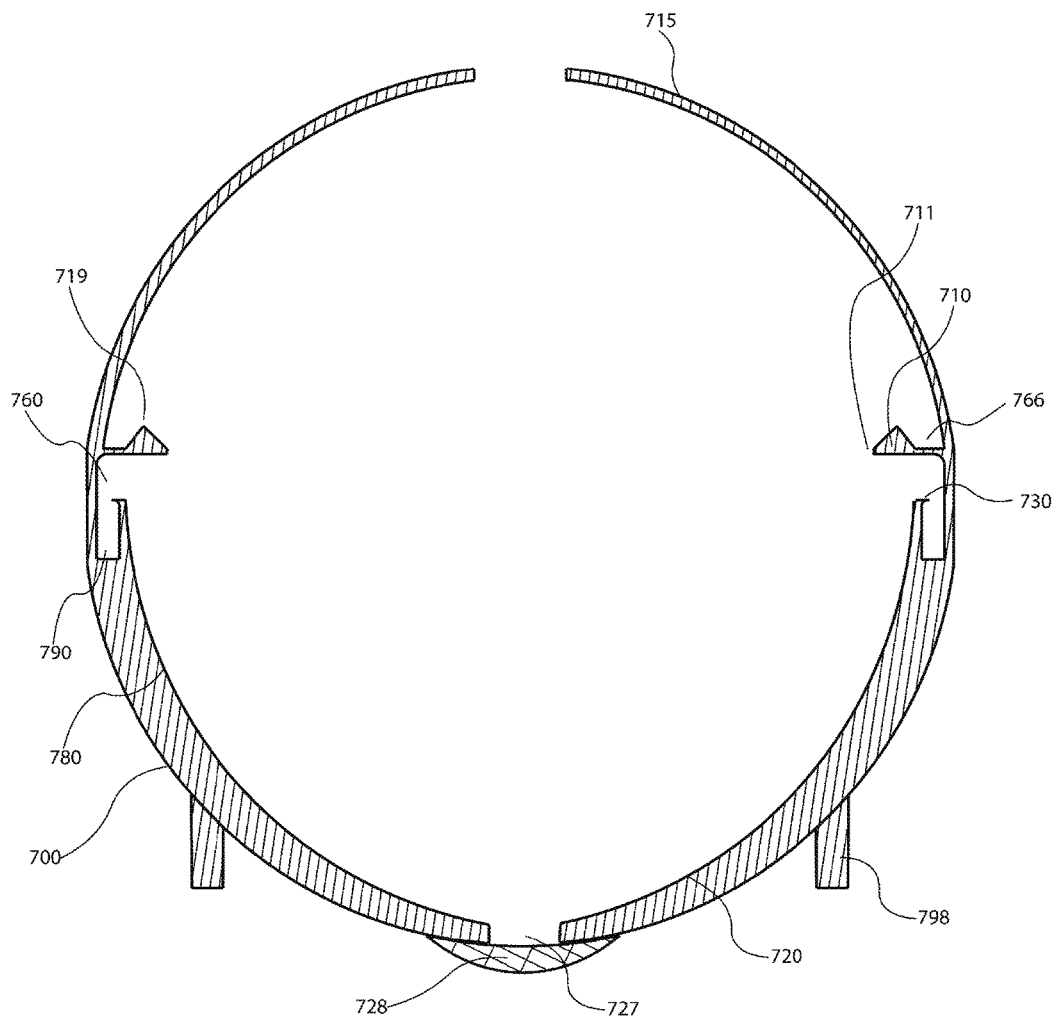
FIG. 7 depicts an illustration of the cross section of a certain embodiment of a hollow spherical device [700] used in the method of this invention. This particular embodiment has a metered vestibule [760] formed by the inward edge [711] of the partial primary lid [710] positioned above the weir [730]. Excess blood will overflow the partial primary lid and flow into the overflow chamber [766] and retained by a retaining weir [719]. The cell-pack will be retained in the trough [790]. An advantage of this design is the steep slope [780] that causes rapid migration of plasma to a drain [727] in the bottom of the bowl [720] that is stoppered with a plug [728]. The partially open upper lid [715] allows an opening through which blood can be pipetted into the hollow sphere. Fixation pins [798] on the lower outer surface of the hollow sphere lock the device into a rotating platform that spins the hollow sphere.

FIG. 7 shows a more complex embodiment of a rotating sphere [700] has a trough [790] and a weir [730] that keeps the cell-pack from sliding down. Manufacturing of this design is more complex but can be done by one skilled in the arts of plastic, metal and ceramic manufacturing. Slotted weirs and baffles can also be added to the sphere design to improve the drainage of plasma while increasing the retention of cell-pack in the trough. We have made embodiments of these spherical designs. A mounting apparatus (FIG. 7, [798]) connects the sphere to the motor. Various types of mounting connections are known to those skilled in the art.

Spinning Conical Devices.

Figure 8:
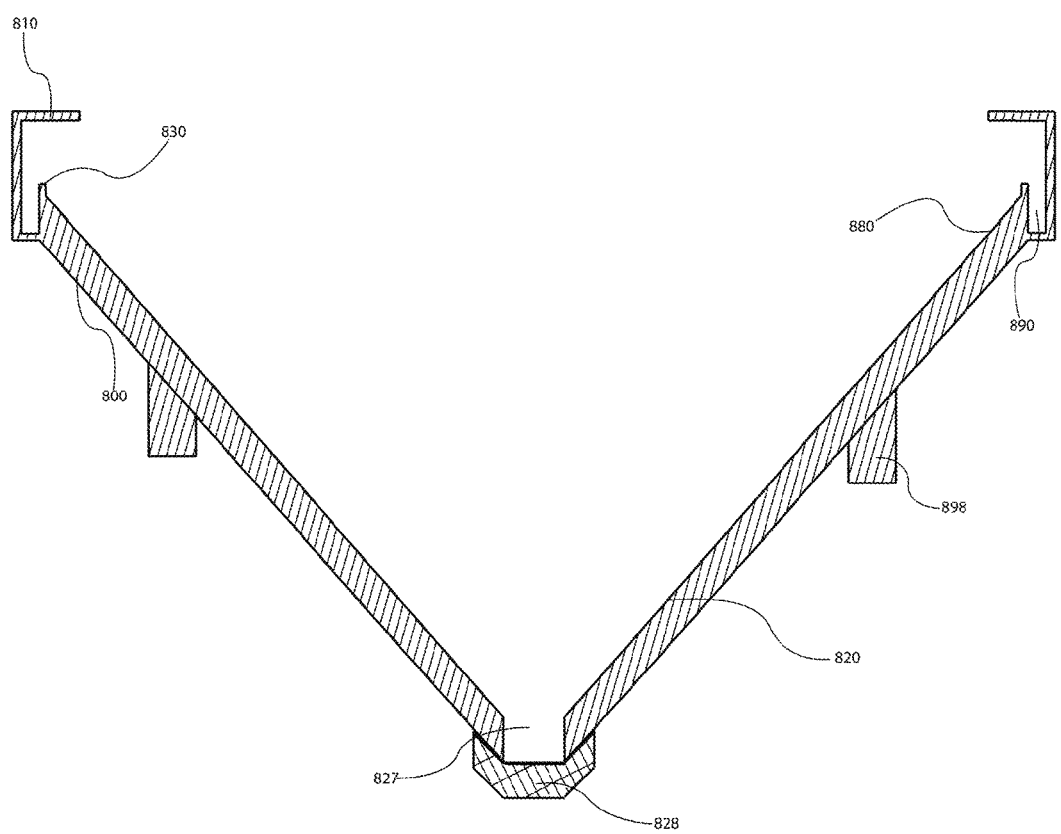
FIG. 8 depicts an illustration of the cross section of a certain embodiment of a hollow conical device [800] used in the method of this invention. This particular embodiment has a partially open primary lid [810] positioned above the weir [830]. Cell-pack can be retained in the trough [890]. An advantage of this design is the steep slope [880] that causes rapid migration of plasma to a drain [827] in the bottom of the bowl [820] that is stoppered with a plug [828]. Fixation pins [898] on the lower outer surface of the hollow cone lock the device into a rotating platform that spins the hollow cone.

Another general shape for a spinning hollow device is that of a cone, an embodiment of which is illustrated in FIG. 8. The upper part of the cone may have a trough [890], lid [810], weir [830], and baffles as found in embodiments of hollow disks. The bowl [820] is in the shape of a cone. This allows plasma to migrate downward to a single central drain [827] at the bottom apex of the cone. This apex may contain a plug or valve [828] actuated by pressure or by other mechanical means. After spinning and migration of plasma to the apex of the cone, the interior of the hollow device can be pressurized to open the valve and push out the separated plasma.

Other Particles in Blood

While an immediately useful application of the methods described in this document is the separation of bacteria from large volumes of blood, the methods described herein could also be applied to the separation of other small particles by sedimentation in a thick film of blood. Such particles might be naturally occurring particles of biological origin, such as platelets, viruses, proteins, microorganisms smaller than RBCs or fragments of cells that sediment more slowly than red blood cells sediment. While there are other techniques used to separate platelets from other blood components, they usually are not as rapid as could be accomplished with the methods described herein. Viruses may be found in blood of persons afflicted with viral blood infections. These microorganisms are much smaller than one micrometer in size scale, and they will have sedimentation velocities much slower than red and white blood cells. These particles can be separated from the blood cells by the methods taught herein. Other particles of biological origin might come from fragments of cells, or from organelles inside cells that may be released when blood cells are mechanically broken or are chemically degraded. Examples may include organelles from white blood cells, which WBCs may have been chemically, biologically or mechanically lysed. These organelles may be mixed with RBCs and other intact WBCs and can be separated by the methods taught herein. There are other particles of biological origin that are not proteins, including lipid molecules and particles containing lipids, and carbohydrate molecules and particles containing carbohydrates. The methods taught herein can be usefully employed to rapidly separate these particles from RBCs and WBCs because their small size will produce a very small sedimentation velocity.

In some instances the small particles in blood may not be of biological origin. Some methods of therapeutic delivery involve placing the therapeutic inside synthetic or natural polymer particles and then injecting them into the blood. The particles may be carbon-based organic particles, or may be inorganic particles such as metals, metal oxides, glasses, ceramics, and more, as known in the art or drug delivery. The separation techniques taught herein may be employed to collect these small therapeutic particles from samples of blood to investigate the extent of drug delivery or the degradation of the particles. If the particles have similar density as blood cells, sedimentation in a thick film in a hollow spinning device may be a very useful and rapid technique to recover these particles for analysis.

Some polymer particles or other particles may be placed in the blood in a diagnostic procedure, such as particles that collect small molecules from the blood by attachment to the particle surface, or particles that undergo a change due to conditions in the blood or body. These diagnostic reporting particles could be injected into the blood, and then after a time, assayed by collecting a few mL of blood and separating the particles from the blood by techniques taught herein. It is even possible that dead bacteria or harmless live bacteria could be injected into the blood as diagnostic reporting particles, when such organisms are modified or genetically engineered to respond to molecules found in the blood or to record body conditions or to attach molecules found in the blood. These diagnostic reporting bacteria could be quickly separated from mL-sized quantities of blood using the methods taught herein.

Other Suspensions of Particles in Fluids

One skilled in the art of separation processes will immediately know that the methods described herein could also be applied to the separation of other small particles by sedimentation within a thick film of the particle suspension. Such particles might be naturally occurring particles of biological origin, as described above, or natural particles of non-biological origin, such as metal particles, ceramic particles, glassy particles, polymer particles, or more. Separation processes for particles have been developed over many years. When the densities of the particles are similar, but the sizes of particles are different, then methods described herein will be particularly useful for rapid batchwise separation of the particles. Nevertheless, any particles that differ in sedimentation velocity can be separated by methods and embodiments of the hollow spinning devices taught herein.

The technology taught herein may be combined with other technologies that may enhance differences in sedimentation velocity. For example the principle of electrophoresis can be used to enhance the difference in sedimentation velocities of charged and non-charged particles by applying an electromagnetic field parallel to or anti-parallel to the centrifugal field in a direction that would slow down slowly-sedimenting charged particles or in a direction that would speed up the sedimentation velocity of fast-sedimenting charged particles. The direction of the field will depend on whether the particles are negatively charged or positively charged. Likewise the difference in sedimentation velocities of non-magnetic particles and particles of magnetic character may be enhanced by applying a magnetic field parallel to the centrifugal field. These principles can be applied by those skilled in the art of colloidal science to practice the invention taught herein.

Utility

The undertaking of the inventive process was driven by a keen need to separate low concentrations of bacteria from blood cells in a rapid and efficient manner. The utility of this invention in this area of medical technology is beyond doubt. Its practice has the potential to save the lives of those with blood infections of unknown origin. The very useful attributes of the technology include: (1) the separation process is very rapid, with separation in less than a minute when the thick film of blood is about 2 mm thick, and is then followed by careful deceleration; (2) large volumes of blood can be processed at once in a batch manner, thus providing higher numbers of bacteria (or particles) when their concentration in blood is very low; (3) unlike isopycnic centrifugation, the method can be used to separate particles of similar density such as bacteria and red blood cells; (4) for the separation of bacteria from blood, the final product is a suspension of bacteria in a filterable liquid, allowing rapid concentration of the bacteria; and (5) the bacteria are still alive at the end of the process, so they can be cultured if needed.

The simplicity of the method also has great utility when it is practiced in a clinical setting. These include: (1) the simple process does not require a skilled operator to carry out the practice of the invention; (2) the simple shape without enclosed or complex flow channels leads to low-cost manufacturing; (3) the low costs of the hollow device allow disposable devices to be affordable, thus reducing the risk involved with cleaning and re-use; and (4) the simple device and method can be easily integrated into a larger process designed to identify the characteristics of the bacteria that is recovered from the blood.

Novelty

The novel aspects of this method of separating bacteria from blood cells or of separating differing particles suspended in a fluid are readily apparent. While separation of bacteria from blood cells has been done in microfluidic channels using very small volumes and volumetric flow rates, separation of bacteria from blood cells has never before been done in large volumes in the large and open format of the hollow spinning device taught herein. One of the unique characteristics of the invention is the formation of a thick film of blood in which separation by sedimentation can be accomplished quickly because of short distances. Another unique characteristic is the use of gravity and a carefully designed trough and weir to passively, without pumps or pressures, allow migration of the cell-pack and plasma to different regions within the hollow device so the separated plasma remains separated and can be easily removed from the hollow device.

Non-Obviousness

There are some very fundamental and key aspects of the present separation system, methd and device that are non-obvious. The most important of these aspects is that the rotating device must be decelerated very carefully to avoid remixing of the separated layers. Particularly as the deceleration nears completion, the rate of deceleration must be very low, as evidenced by the data in FIG. 9. The hollow device must also spin very stably, without wobble or other vibrations, which vibrations will cause remixing of the layers near the end of the deceleration.

Some aspects of the weir design were non-obvious and were discovered after experimentation and trial iterations on design. For example, the placement of baffles that extend from the vestibule to the slope is non-obvious. The placement of fillets in the corners of the vestibule is also considered non-obvious, at least until the hollow device was actually built and scrutinized carefully during flow-down of the plasma.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described methods, features, structures, or characteristics of the invention may be combined in any suitable manner in one or more embodiments. In the following description of examples, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

The present invention and methods may be embodied in other specific forms without departing from its spirit or essential characteristics. The described embodiments are to be considered in all respects only as illustrative and not restrictive. The scope of the invention is, therefore, indicated by the appended claims rather than by the description and examples. All changes that come within the meaning and range of equivalency of the claims are to be embraced within their scope.

EXAMPLES

We present several examples of various aspects of the invention and methods pertaining to the separation of slow-sedimenting particles from fast-sedimenting particles.

Example 1: Bacteria from Blood with Very Low CFU/mL, Using a Protruding Weir

A 12-cm-diameter hollow device was built in a disk shape, composed of photopolymerizable acrylates (Vero-Clear™ Resin), polymerized using a rapid-prototyping system (Stratasys Objet30 Prime, Eden Prairie, Minn., USA). The disk was radially symmetric and designed to spin around a central axis. The surface of the disk radially inward of the weir resembled a bowl with a downward slope toward the center of the disk. The disk was designed so that when the spinning disk slows to a stop, the separated plasma layer drains towards the bowl around the center of the disk. The hollow device was designed with a retaining weir to hold back the cell-pack while the plasma migrated to the bowl of the disk. The volume of the vestibule from slightly inside of the innermost edge of the weir to the back wall of the vestibule was 8.50 mL. The outward edge of the top of the weir protruded into the trough, as shown in FIG. 1. The inward edge of the weir was designed with a sharp corner leading into a downward concave slope designed to quickly drain the plasma toward the bowl. The hollow disks were designed to hold 3.5 mL in the trough, outward from and below the top of the weir. The disk was designed with a partial lid at the top of the vestibule such that 8.5 mL of fluid occupied the vestibule volume, which volume is defined to be from 71 μm inward of the front inward corner of the weir, up to the lid, back to the back wall and down into the trough. The volume displaced by the windowed baffles was accounted for when designing the vestibule. When 8.5 mL of slightly diluted blood was spun into the vestibule, the inward facing upper corner of the slope and the weir was wetted with a layer of blood about 71 μm thick. The partial lid was open in the middle so PBS and blood were easily be pipetted in, and recovered plasma withdrawn. The baffles did not extend to the bottom of the trough so this hollow disk device could be easily cleaned from cell-pack and reused.

This disk was designed with 16 triangular baffles extending from the corner between the back wall of the vestibule and the lid, extending downwards and inwards into the bowl. The baffles were of uniform thickness and had triangular cutout windows originating from the back wall of the vestibule and extending to the outward tip of the protruding weir (see FIG. 2), which allowed for fluid circulation in the vestibule during the spinning process. The baffles did not extend to the bottom of the trough behind the weir, thus allowing circulation in the trough. The corners between the baffles and the rear wall of the upper region of the vestibule were filleted with a radius of 0.25 mm. The corner between the rear wall and lid was filleted with a radius of 1.28 mm. There was no filleting at the intersections of the slanted baffles with the weir or with the surface of the slope.

The disks were mounted onto a 3D printed platform that was connected by press fit to the spindle of a compact disc (CD) motor (OT-11400 CD spindle motor, Wagner Electronics Super Store, Ashfield, Australia).

The CD motor was controlled by the following system. The output of an Arduino Uno (ATmega 328P) microcontroller (powered with a 12 v power supply) was routed through a L298N stepper motor driver (DROK Electronics) and into a KP4M-023 stepper motor (Japan Servo Co.). This stepper motor was directly attached to the output control dial of a KPS 620M power supply (KEPCO INC, Sanford, N.Y.) via adhesive tape. The positive and negative terminals of the KEPCO power supply were directly connected to the OT-11400 CD spindle motor used to spin the hollow device. This arrangement allowed for programmable changes in the Arduino to repeatedly and precisely control the voltage output, and the corresponding rotational velocity of the disk. The disk velocity was measured by a tachometer (Extech Instruments, model 461920, Nashua, N.H.).

Phosphate buffered saline (PBS, without calcium) was made from salts purchased from Sigma Aldrich (St. Louis, Mo.) and Fisher Scientific (Fair Lawn, N.J.). PBS was sterilized by autoclaving.

Sodium dodecyl sulfate (SDS, Acros Organics, Fair Lawn, N.J.) was dissolved into distilled deionized water (DDH2O) at ~50° C. and then cooled to make a 15% stock solution.

Ethanol for sterilizing the spinning hollow disk was made by diluting 95% denatured ethyl alcohol (Fisher Chemical, Fair Lawn, N.J.) with sterile water to a final concentration of 70% by volume.

*Escherichia coli* (*E. coli*, strain BL-21 Star DE3) was streaked from frozen culture onto a nutrient agar plate (DIFCO Sparks, Md.) and incubated at 37° C. for 24 hours. From this plate, a single colony was inoculated into 1 mL of nutrient broth (DIFCO Sparks, Md.) in a sterile test tube. After shaking for 8 hours at 200 rpm at 37° C., this 1-mL bacteria suspension was transferred to 50 mL of nutrient broth in a 250 mL sterile shaker flask. This flask was shaken for another 16 hours at 200 rpm and 37° C. The bacteria was collected by centrifugation and washed twice with sterile PBS. The bacterial concentration was estimated by optical density at 600 nm using a spectrophotometer. The bacteria were then diluted with sterile PBS to form a stock solution of 480 CFU/mL.

Following an approved protocol, blood was collected on the day of the experiment from a healthy female donor into 10 mL EDTA anti-coagulant tubes (Vacutainer #366643, Becton Dickinson, Franklin Lakes, N.J.). The blood was stored at 4° C. until about an hour before experiments, at which time it was warmed to room temperature. Immediately before experiments, the Vacutainer tubes were inverted several times by hand and 8.0 mL of blood was pipetted into a sterile test tube. Then 100 μL of the *E. coli* stock solution was added to the blood and mixed by lightly vortexing for 10 seconds.

Before spinning, the hollow device was washed with water, sterilized with 70% ethanol, and dried with clean compressed air. Then 7.0 mL of the blood and bacteria mixture were pipetted into the hollow disk, and 1.5 mL sterile PBS was pipetted as uniformly as possible into the pool of blood. Immediately the disk was accelerated for 22 seconds to 3000 rpm and held at that speed for 38 seconds. The disk was then decelerated from 3000 to 300 rpm over 65 seconds, and then decelerated linearly from 300 to 0 rpm over a time of 240 seconds. There was no remixing of cell-pack and plasma. When the disk came to rest, the plasma, which contained some bacteria, drained into the bowl of the disk. There was a small amount of streaking of red color into the amber-colored plasma. All of the plasma that flowed down was pipetted into a pre-weighed sterile test tube. The tube was weighed again to determine the weight of the plasma, which was converted to a volume of plasma assuming a density of 1.024 g/mL. In three replicates, the volumes of recovered plasma were 4.33, 4.60 and 4.31 mL.

The bacteria in the recovered plasma were collected by filtration and the colony forming units (CFUs) were quantified as follows. First, to preclude hemoglobin-containing red blood cells from collecting on the filter, the red blood cells were weakened by diluting the recovered plasma 1:10 (by volume) with distilled deionized water (DDH2O). Then sodium dodecyl sulfate (SDS) was added from a stock solution of 15% (w/v) to produce a final concentration of 0.025% (w/v) SDS in the diluted plasma solution. The subsequently described sterile vacuum filtration system had already been placed in a sterile laminar flow hood. A 47-mm black filter with 0.45-μm pore size (MSP000814, EMD Millipore, Billerica, Mass.) was placed on the porous metal filter connected to a Microfil Filtration System (1217N109, EMD Millipore, Billerica, Mass.). The membrane filter was sandwiched between the metal filter and a 100-mL Microfil funnel (EMD Millipore, Billerica, Mass.) and wetted with sterile PBS. The vacuum was turned on. An aliquot of the recovered plasma was pipetted onto the filter, and the liquid was pulled through the filter with vacuum suction. This was followed by a rinse of sterile PBS. The filtration process was spread over 3 filters and funnels to avoid clogging the filter with cell debris. There was no red color observed on the filters, suggesting that the residual RBCs had broken during or before the filtration process and the hemoglobin had passed through the filters. The filters were carefully removed and placed onto nutrient agar plates and the bacteria was allowed to grow for 48 hours at 37° C., after which the colonies were counted. In these 3 replicates, the colony counts were 24, 21 and 47 CFUs.

Calibration of stock solution. To calculate the efficiency of bacterial recovery from the recovered plasma, we had to calculate as precisely as possible the number of bacteria added to the blood, and the number of bacteria in the blood placed on the hollow device. This calculation started with measuring the CFUs/mL in the dilute stock solution in PBS that was used to inoculate the blood. The same volume of dilute stock solution (100 µL) that was inoculated into 8.0 mL of blood was inoculated into 8.0 mL of centrifuged clear plasma obtained from the blood of the same donor. Thus any inhibition or promotion of growth due to plasma proteins would be consistent in the experimental and calibration samples. To prepare the centrifuged plasma, two tubes containing 8 mL of blood each were spun in a centrifuge (Horizon Model 642E, Fisher HealthCare, Fair Lawn, N.J.) at 3328 rpm for 20 minutes. Then 4.0 mL of clear plasma were pipetted off each tube and combined to place 8.0 mL in a sterile container. To this 8.0 mL of centrifuged plasma, 100 µL of the stock bacterial suspension was added to bring the bacterial concentration to match the bacterial concentration prepared in the 8.0 mL of whole blood used for the sedimentation experiments. After an hour, this centrifuged and spiked plasma was diluted 1:10 with DDH2O; then SDS was added from a stock solution of 15% (w/v) to make the final concentration of 0.025% (w/v) SDS in the diluted plasma solution. The entire plasma sample was divided into aliquots, and each aliquot was vacuum filtered and the filters were grown on plates as described previously in this example for growing bacteria from the recovered plasma. The numbers of bacterial colonies on each filter were summed to calculate the CFU/mL of the stock suspension of bacteria. From knowledge of the stock solution concentration and knowledge that 100 µL of stock solution was pipetted into 8.0 mL of blood, the amount of CFUs pipetted onto the hollow device in 7.0 mL of blood was calculated. In these replicates, the stock solution contained 480 CFU/mL, the concentration in the blood was 6 CFU/mL, and the number of CFUs pipetted into the hollow device was 42. In these 3 replicates, the percentage of bacteria in the recovered plasma and collected on the filter was 57, 50 and 112%, producing an average of 73% recovery of CFUs from the bacteria-spiked blood sample.

Example 2: Bacteria from Blood with Low CFU/mL, Using a Protruding Weir

Example 2 used the same method and same hollow device and same spinning control system as described in Example 1, the only difference being that male blood was used, and the concentration of the bacterial stock solution was determined to be 16,480 CFU/mL. This produced a spiked blood concentration of 206 CFU/mL. In 4 replicates, the percentage of bacteria recovered from the plasma and collected on the filter was calculated as 67%, 69%, 69% and 79%, producing an average of 71% recovery of CFUs in the original blood sample.

Example 3: Plasma Flow-Down, with and without Diluent, Protruding Weir

In this study, experiments were done to determine if adding a PBS diluent to the blood changed the amount of plasma that could be recovered after rotation. The same control and spinning system were used as described in Example 1. One set of experiments used 8.5 mL of female whole blood, and the other set of experiments used 7.0 mL of blood from the same volunteer mixed with 1.5 mL of PBS. No bacteria were added, as we were only interested in the volumes of recovered plasma. EDTA was the anticoagulant.

When spinning commenced the blood was quickly spun into the vestibule, forming a blood layer of 2 mm thick. The disk was accelerated for 22 seconds to 3000 rpm and held at that speed for 38 seconds, during which time two distinct vertical layers were observed to form, a transparent amber-colored plasma layer and a darker red-colored cell-pack layer. Then the hollow disk device was decelerated from 3000 to 300 rpm over 65 seconds, and then decelerated linearly from 300 to 0 rpm over a time of 240 seconds. There was no remixing of cell-pack and plasma. When the hollow disk came to rest, some plasma drained into the bowl of the disk. The plasma that flowed down from the weir was collected by pipetting into a pre-weighed sterile tube, which was weighed. The weight of the plasma was calculated and recorded. The calculated volume of the plasma was recorded.

For the experiment using 8.5 mL of whole blood, the amount of plasma recovered was 3.0, 3.3 and 3.5 mL; the average recovery volume was 3.3 mL. For the experiment using 7.0 mL of whole blood and 1.5 mL of PBS, the amount of plasma recovered was 4.5, 4.3 and 2.9 mL; the average recovery volume was 3.9 mL.

Examples 4-7: Weir Designs to Investigate Streaking

Examples 4, 5, 6 and 7 are examples of experiments in which qualitative assessment of streaking was done to provide data for improved design of the hollow device. Male blood was spun using 12-cm-diameter hollow disk devices of the general design of FIG. 1, but with variations to baffles and the weir. The blood was not spiked with bacteria, as the assessment was of cell-pack streaking, not bacterial recovery. The amount of streaking of red-colored cell-pack into the plasma was qualitatively assessed on a scale of 0 to 5 as follows. 0: no streaking observed; 1: very light streaking in the form of short thin wisps of red color; 2: more streaking manifest by longer and thicker lines of red color; 3: even thicker lines of red color flowing down and forming smaller pools of red color; 4: very thick lines of red color flowing down and forming larger pools of red color; 5: greater than 80 of the flow-down contaminated with red color.

Example 4: Plasma Clarity with No Baffles Using a Rectangular Trough

In this example, spinning of the hollow device was controlled by the following system. The negative terminal of a KPS 620M power supply (KEPCO INC, Sanford, N.Y.) was directly connected through a common ground to a OT-11400 CD spindle motor (Wagner Electronics Super Store, Ashfield, Australia) that was used to spin the hollow device. The positive terminal of the KPS 620M power supply was connected to a 10-ohm variable resistor (Honeywell Clarostat, model 3410234, El Paso, Tex.). The variable resistor positive terminal was then connected to the positive terminal of the CD spindle motor. Two pieces of reflective tape were placed opposite each other on the sides of the hollow device. The voltage dials on the KEPCO power supply, as well as the resistance dial on the variable resistor were manually manipulated by an operator to achieve the desired maximum speed and slowdown rate of the disk, as measured continuously by a photo tachometer (Extech Instruments, model 461920, Nashua, N.H.). The combination of the power supply and variable resistor allowed a skilled operator to have fine tuning and control during the acceleration, holding at the desired angular velocity (rpm) and decelerating the hollow device.

Seven mL of male blood was placed in an embodiment of a hollow device. The hollow device was accelerated to 3,000 rpm over 22 seconds, held at this speed for 38 seconds, and then decelerated by turning off the power to the CD motor. The resultant "coasting" deceleration profile followed that described in Example 1, and produced no remixing of the separated plasma and cell-pack. Several repeats of the experiments with this disk were done.

In this example, the 12-cm-diameter hollow disk device had no baffles and no protruding lip on the weir, and the trough had a rectangular cross section.

Near the end of deceleration we noted that surface tension between the plasma and the surface of the weir produced a bulging meniscus. In some cases, it took several seconds after cessation of spinning for the plasma to finally "break through" the meniscus and flow down. The plasma always flowed down from the single "break through" point. The streaking was rated a level 4, producing a large pool of red color that flowed down with the plasma. We supposed that when "break-through" only occurred at one point, the plasma, which was flowing circumferentially in the upper portion of the vestibule to the break-through point, entrained some cell-pack along the way and produced heavy streaking. We also noted that there was still much plasma hanging in the upper back corner of the vestibule.

Example 5: Plasma Clarity, 8 Baffles, Rectangular Trough

In this example, the spinning control system was the same as in Example 4. Seven mL of male blood was placed in a different embodiment of a hollow device. The device was accelerated to 3,000 rpm over 22 seconds, held at this speed for 38 seconds, and then decelerated by turning off the power to the CD motor. The resultant "coasting" deceleration profile followed that described in Example 1. Several repeats of the experiments with this hollow device were done.

In this example, the 12-cm-diameter hollow disk device had no protruding lip on the outward edge of the weir, and the trough had a rectangular cross section. There were 8 rectangular baffles that extended from the inward edge of the weir to the lid and back into the trough and extending to the bottom of the trough. The inward edge of the baffle was vertical.

Near the end of deceleration we noted that surface tension between the plasma and the surface of the weir produced a bulging meniscus. However, just before or sometimes at the cessation of spinning the plasma started to flow down. The flow originated from 2 or 3 points, each where baffles connected to the weir. There was red streaking that appeared to originate from both sides of the baffles, forming 2 parallel streaks. The level of streaking ranged from 2 to 3. We hypothesized that baffles provided a point of initiation for flow-down. We also noted that there was still much plasma hanging in the upper back corner of the vestibule and in the corners formed by the baffles connecting to the back wall of the vestibule and connecting to the lid. The disk was difficult to clean owing to the baffles in the trough.

Example 6: Plasma Clarity with 16 Baffles Using a Rectangular Trough

In this example, the spinning control system was the same as in Example 4. Seven mL of male blood was placed in a different embodiment of a hollow device. The device was accelerated to 3,000 rpm over 22 seconds, held at this speed for 38 seconds, and then decelerated by turning off the power to the CD motor. The resultant "coasting" deceleration profile followed that described in Example 1.

In this example, the 12-cm-diameter hollow disk device had no protruding lip on the weir, and the trough had a rectangular cross section. There were 16 rectangular baffles that extended from the inward edge of the weir to the lid and back into the trough to the bottom of the trough with no windows. Several repeats of the experiments with this hollow device were done.

Near the end of deceleration we noted that surface tension between the plasma and the surface of the weir produced a bulging meniscus. However, just before the cessation of spinning the plasma started to flow down. The flow originated from 6 to 8 points, each where baffles connected to the weir. There was red streaking that appeared to originate from both sides of the baffles, forming 2 parallel streaks. The level of streaking ranged from 1 to 2. We hypothesized that baffles provided a point of initiation for flow-down. The difficulty in using this disk design was that it was onerous and time-consuming to clean all of the cell-pack from the trough with all the baffles extending to the bottom of the trough. We also noted that there was visible plasma retained in the corners made by intersection of the baffles with the lid and with the back wall of the vestibule, as well as plasma in the upper corner of the lid and back wall of the vestibule.

Example 7: Plasma Clarity Using Triangular Baffles with Windows and a Protruding Weir In this example, the spinning control system was the same as in Example 4. Seven mL of male blood was placed in a different embodiment of a hollow device. The device was accelerated to 3,000 rpm over 22 seconds, held at this speed for 38 seconds, and then decelerated by turning off the power to the CD motor. The resultant "coasting" deceleration profile followed that described in Example 1.

In this example, the spinning hollow device was the same as described in Example 1, having 16 triangular baffles, extending into the bowl beyond the inward edge of the weir, and connecting to the bowl, having triangular windows in the upper vestibule region, and a rectangular window at the bottom of the trough. Also the outward edge of the top of the weir protruded into the trough, as shown in FIG. 2. The corners between the baffles and the rear wall of the upper region of the vestibule were filleted with a radius of 0.25 mm. The corner between the rear wall and lid was filleted with a radius of 1.28 mm. There was no filleting at the intersection of the slanted baffles with the weir or with the surface of the slope. Several repeats of the experiments with this hollow device were done.

Near the end of deceleration we noted that surface tension between the plasma and the surface of the weir produced a bulging meniscus except where the baffles cut across the weir and extended into the bowl. Just before the cessation of spinning the plasma started to flow down. The flow originated from 6 or more points, each point where baffles crossed the weir. Sometimes very thin red streaking appeared only near the end of flow-down. It originated from both sides of the baffles, forming 2 parallel wispy streaks of short length. The level of streaking generally was 0 for female blood and 1 for male blood. We hypothesized that baffles provided a point of initiation for flow-down. We hypothesized that female blood, with generally lower hematocrit, formed a cell-pack whose volume was smaller than the volume of the trough, and that the cell-pack remained totally confined in the trough. Male blood, with a generally greater hematocrit, formed a cell-pack whose volume was not much, if at all, smaller than the volume of the trough, and so some small amount of cell-pack was entrained with the last of the plasma flowing down. We hypothesized that when the cell-pack slid down the back wall of the vestibule at the end of deceleration, the protruding weir directed the flow of cell-pack away from the weir, which reduced the amount of streaking. There was no difficulty cleaning all of the cell-pack from the trough. We did not observe any plasma retained in any corners of the upper section of the vestibule.

Example 8: Short Spinning Time Produces Poor Separation of RBCs

In this example the time of rotation was not long enough for good sedimentation of RBCs from the layer of plasma into the cell-pack. Thus many RBCs were in the recovered plasma.

In this example, the hollow rotating device was that described in Example 1. The rotation of the hollow device was controlled by the following system. The motor driving this system was a Maxon 301039 Combination brushless DC motor (Maxon Motor Co. Sachseln, Switzerland). The rotational speed of the motor was read via an HEDL-5540 A12 digital encoder attached to the motor. The output signal from the HEDL digital encoder was wired into a cRIO 9074 FPGA board (National Instruments, Austin, Tex.) through an 9411 DAQ module (National Instruments, Austin, Tex.), which was powered by a GPS 3030D power supply (GW Instek Co., Taipei, Taiwan.) This signal was then processed by the FPGA board via a LabVIEW-based PID controller. An analog control voltage between 0-10V (based on the PID control calculations) was then transmitted via a 9263 DAQ module (National Instruments, Austin, Tex.), also attached to the cRIO FPGA board, to a CBE12A1C brushless PWM servo amplifier (Advanced Motion Controls, Camarillo, Calif.). The PWM servo amplifier, supplied with 30V from a GPS 2303 laboratory power supply (GW Instek Co., Taipei, Taiwan.), drove the Maxon 30103 motor according to the 0-10V signal coming from the FPGA, 0V corresponding to a resting state and 10V corresponding to a maximum motor speed.

In this example, blood was collected from a female donor into EDTA anti-coagulant vacutainer tubes. Eight mL of blood was placed in a sterile test tube.

100 µL of diluted *E. coli* stock solution was pipetted into the 8.0 mL of blood in the sterile tube. The tube was capped and gently inverted by hand several times for about 10 seconds to ensure good mixing. This produced a concentration of around $5.6 \times 10^5$ CFU/mL, which was subsequently quantified more exactly by serial dilution of the blood and by plate counting, a common technique known to those in the art.

After a tube of blood was spiked with bacteria, 7.0 mL of the blood was pipetted onto the bowl of the disk, and 1.5 mL of PBS was pipetted into the pool of blood in the bowl of the disk. Spinning commenced immediately. The blood was quickly spun into the vestibule, forming a blood layer of 2 mm in thickness. The disk was accelerated for 12 seconds to 3000 rpm and held at that speed for 33 seconds, during which time two distinct vertical layers were observed to start to form, a transparent amber-colored plasma layer and a darker red-colored cell-pack layer. Then the hollow disk device was decelerated from 3000 to 300 rpm over 65 seconds, and then decelerated linearly from 300 to 0 rpm over a time of 240 seconds. There was no remixing of cell-pack and plasma. When the hollow disk came to rest, some plasma, which contained some bacteria, drained into the bowl of the disk. The plasma was orange throughout, not amber colored as observed in Examples 1 and 2. There was no separation of colors in the pool of the recovered plasma. The plasma that flowed down from the weir was collected by pipetting into a pre-weighed sterile tube, which was weighed. The weight of the plasma was converted to a volume of the plasma.

The bacterial CFU concentrations (CFU/mL) in the recovered plasma were also determined by serial dilution and plating. The total CFUs in blood placed in the hollow disk was calculated as the product of the whole blood CFU/mL multiplied by the volume of blood pipetted into the disk (7.0 mL). The number of bacterial CFUs recovered in the plasma was calculated as the multiplication product of the plasma CFU/mL multiplied by the volume of plasma recovered from each experiment. The percentage of bacterial recovery was calculated as the CFUs recovered in plasma divided by the CFUs in the blood pipetted into the hollow disk, multiplied by 100%.

Quantitation of RBCs in the whole blood or in recovered plasma was done indirectly by measuring the amount of hemoglobin (Hb) in the sample as follows. In calibration experiments, blood was diluted in PBS and the red blood cells were counted with a hemocytometer. The optical densities of these samples were measured at 280, 421 and 600 nm wavelengths on a UV/vis spectrometer. A correlation function was generated that related the hemocytometer counts of RBC concentration to the optical density values at 280, 421 and 600 nm. The RBC concentrations in the original blood ($RBC_{blood}$) and in the recovered plasma ($RBC_{plasma}$) were calculated from this correlation. The percentage of removal of red blood cells was calculated from $(1-RBC_{plasma}/RBC_{blood}) \times 100\%$.

Platelet concentration in recovered plasma was measured by diluting and photographing (Zeiss, Axiocam 105) with a microscope (Olympus, BH2-UMA) the recovered plasma. Platelets were counted from digitized photographs using ImageJ software (NIH) and our own custom data analysis software. These values were converted to a number of platelets per milliliter of recovered plasma.

For these experiments the amount of plasma recovered was 3.7 mL, and there were no streaks observed coming from the baffles. The percent bacterial recovery was 42.2%, but only 91.7% of the RBCs were removed. The platelet concentration was $4.0 \times 10^8$/mL.

Example 9: Example with Higher Angular Velocity

In this example the time of rotation was short, but the angular velocity was high enough for good sedimentation of cells into the cell-pack. Thus fewer RBCs were recovered in the plasma than in Example 8.

In this example, the hollow rotating device was the same as described in Example 8. The rotation system was the same as in Example 8.

In this example, blood was collected from a male donor into EDTA anti-coagulant vacutainer tubes. Eight mL of blood were placed in a sterile test tube.

100 µL of diluted *E. coli* stock solution was pipetted into the 8.0 mL of blood in the sterile tube. The tube was capped and gently inverted by hand several times for about 10 seconds to ensure good mixing. This produced a concentration of around $9.3 \times 10^3$ CFU/mL, which was subsequently quantified more exactly by serial dilution of the blood and by plate counting, a common technique known to those in the art.

After a tube of blood was spiked with bacteria, 7.0 mL of the blood was pipetted onto the bowl of the disk, and 1.5 mL of PBS was pipetted into the pool of blood in the bowl of the disk. Spinning commenced immediately. The blood was quickly spun into the vestibule, forming a blood layer of 2 mm in thickness. The disk was accelerated for 16 seconds to 4000 rpm and held at that speed for 29 seconds, during which time two distinct vertical layers were observed to form, a transparent amber-colored plasma layer and a darker red-colored cell-pack layer. Then the hollow disk device was decelerated from 4000 to 300 rpm over 85 seconds, and then decelerated linearly from 300 to 0 rpm over a time of 240 seconds. There was no remixing of cell-pack and plasma. When the hollow disk came to rest, some plasma, which contained some bacteria, drained into the bowl of the disk. The plasma was amber colored with some streaking from the baffles. The plasma that flowed down from the weir was collected by pipetting into a pre-weighed sterile tube, which was weighed. The weight of the plasma was calculated and recorded, as was the calculated volume of the plasma.

The bacterial concentrations and recovery were done as in Example 8.

Quantitation of RBCs was done as described in Example 8.

Quantitation of platelets was done as described in Example 8.

For this experiment the amount of plasma recovered was 4.5 mL, and there were streaks observed at a streaking level of 2. The percent bacterial recovery was 38.7%, and 99.4% of the RBCs were removed. The number of platelets was $2.6 \times 10^8$/mL.

Example 10: Citrate and Heparin, Both with ADP

This example teaches the use of citrate and heparin as anticoagulants, and the use of ADP as a platelet aggregant. These experiments used the same hollow device and the same spinning control system and same bacterial species as in Example 1. The bacteria was collected by centrifugation and washed twice with sterile PBS. The bacterial concentration was estimated by optical density at 600 nm using a spectrophotometer. The bacteria were then diluted with sterile PBS to form a stock solution of about $5.7 \times 10^7$ CFU/mL.

In this example, blood was collected from one female donor into heparin anti-coagulant vacutainer tubes (Becton Dickinson #363083 tubes, 10 mL) and citrate anti-coagulant vacutainer tubes (Becton Dickinson #367874, 4 mL tubes), respectively. Eight mL of each type of anticoagulated blood was placed in separate sterile test tubes.

100 µL of diluted *E. coli* stock solution was pipetted into the 8.0 mL of blood in each sterile tube (either citrated blood or heparinized blood). Also 115 µL of 1.1 mg/mL ADP in sterile PBS was added to each tube. The ADP was obtained from Sigma-Aldrich in powder form. Fresh ADP solution was prepared the day of use. The tubes were capped and gently inverted by hand several times for about 10 seconds to ensure good mixing. This produced a concentration of around $7.2 \times 10^5$ CFU/mL, which was subsequently quantified more exactly by serial dilution of the blood and plate counting, a common technique known to those in the art.

After a tube of blood was spiked with bacteria and ADP, 7.0 mL of bacteria-spiked blood was pipetted onto the bowl of the disk, and 1.5 mL of PBS was pipetted into the pool of blood in the bowl of the disk. Spinning commenced immediately. The blood was quickly spun into the vestibule, forming a blood layer of 2 mm thickness. The disk was accelerated for 22 seconds to 3000 rpm and held at that speed for 38 seconds, during which time two distinct vertical layers were observed to form, a transparent amber-colored plasma layer and a darker red-colored cell-pack layer. Then the hollow disk device was decelerated from 3000 to 300 rpm over 65 seconds, and then decelerated linearly from 300 to 0 rpm over a time of 240 seconds. There was no remixing of cell-pack and plasma. When the hollow disk came to rest, some plasma, which contained some bacteria, drained into the bowl of the disk. With heparinized blood, there was in this case a small amount of streaking of red color into the amber-colored plasma. All of the plasma that flowed down was pipetted into a pre-weighed sterile test tube. The tube was weighed again to determine the weight of the plasma, which was converted to a volume of plasma assuming a density of 1.024 g/mL.

The bacterial CFU concentrations (CFU/mL) in the recovered plasma and the percentage of bacterial recovery were measured as described in Example 8.

Quantitation of RBCs in the whole blood or in recovered plasma and the calculation of RBC removal was done as described in Example 8.

The platelet concentration was done as described in Example 8.

For the experiment using female citrated blood with ADP, the amount of plasma recovered was 3.3 mL, and the streaking value was zero. The percent bacterial recovery was 33%, and 99.7% of the RBCs were removed. The platelet concentration in the recovered plasma was $4.1 \times 10^7$ platelets/mL. For the experiment using female heparinized blood with ADP, the amount of plasma recovered was 4.0 mL, with a streaking value of 1. The percent bacterial recovery was 50%, and 98.0% of the RBCs were removed, respectively. The platelet concentration in the recovered plasma was $3.0 \times 10^8$ platelets/mL.

Example 11: Heparinized Blood, with and without ADP

This example teaches the use of ADP to reduce the number of platelets in the recovered blood. This example used the same hollow device and the same spinning control system and same bacterial species as in Example 1. The bacteria was collected by centrifugation and washed twice with sterile PBS. The bacterial concentration was estimated by optical density at 600 nm using a spectrophotometer. The bacteria were then diluted with sterile PBS to form a stock solution of about $5.7 \times 10^7$ CFU/mL.

In this example, blood was collected from one female donor into heparin anti-coagulant vacutainer tubes (Becton Dickinson #363083 tubes, 10 mL).

Two sterile tubes containing 8.0 mL of heparinized blood were prepared. To each was added 100 µL of diluted *E. coli* stock solution. To only one of the tubes was added 115 µL of 1.1 mg/mL ADP in sterile PBS. The tubes were capped and gently inverted by hand several times for about 10 seconds to ensure good mixing. This produced concentrations of around $7.2 \times 10^5$ CFU/mL and $7.3 \times 10^5$ CFU/mL with and without ADP, respectively, which concentrations were subsequently quantified more exactly by serial dilution of the blood and plate counting, a common technique known to those in the art.

After a tube of blood was inverted by hand, 7.0 mL of bacteria-spiked blood was pipetted onto the bowl of the disk, and 1.5 mL of PBS was pipetted into the pool of blood in the bowl of the disk. Spinning commenced immediately. The blood was quickly spun into the vestibule, forming a blood layer of 2 mm thickness. The disk was accelerated for 22 seconds to 3000 rpm and held at that speed for 38 seconds, during which time two distinct vertical layers were observed to form, a transparent amber-colored plasma layer and a darker red-colored cell-pack layer. Then the hollow disk device was decelerated from 3000 to 300 rpm over 65 seconds, and then decelerated linearly from 300 to 0 rpm over a time of 240 seconds. There was no remixing of cell-pack and plasma. When the hollow disk came to rest, the plasma, which contained some bacteria, drained into the bowl of the disk. All of the plasma that flowed down was pipetted into a pre-weighed sterile test tube. The tube was weighed again to determine the weight of the plasma, which was converted to a volume of plasma assuming a density of 1.024 g/mL.

The bacterial CFU concentrations (CFU/mL) in the recovered plasma and the percentage of bacterial recovery were measured as described in Example 8.

Quantitation of RBCs in the whole blood or in recovered plasma and the calculation of RBC removal was done as described in Example 8.

Platelet concentrations were calculated as described in example 8.

For the experiment using female heparinized blood without ADP, the amount of plasma recovered was 4.2 mL, and the streaking value was 2. The percent bacterial recovery was 46%, and 91.7% of the RBCs were removed. The platelet concentration in the recovered plasma was $1.3 \times 10^9$ platelets/mL. For the experiment using female heparinized blood with ADP, the amount of plasma recovered was 4.0 mL, with a streaking value of 1. The percent bacterial recovery was 50%, and 98.0% of the RBCs were removed, respectively. The platelet concentration in the recovered plasma was $3.0 \times 10^8$ platelets/mL.

Example 12: Recovery of Very Low Concentrations of *E. cloacae*

Example 12 used the same method and same hollow device and spinning control system as described in Example 1. PBS, SDS and 70% ethanol were prepared as described in Example 1.

*Enterobacter cloacae* (*E. cloacae*, strain ATCC 13047) was streaked from frozen culture onto a nutrient agar plate (DIFCO Sparks, Md.) and incubated at 37° C. for 24 hours. From this plate, a single colony was inoculated into 1 mL of nutrient broth (DIFCO Sparks, Md.) in a sterile test tube. After shaking for 8 hours at 200 rpm at 37° C., this 1-mL bacteria suspension was transferred to 50 mL of nutrient broth in a 250 mL sterile shaker flask. This flask was shaken for another 16 hours at 200 rpm and 37° C. The bacteria was collected by centrifugation and washed twice with sterile PBS. The bacterial concentration was estimated by optical density at 600 nm using a spectrophotometer. The bacteria were then diluted with sterile PBS to form a stock solution of 9,408 CFU/mL.

Blood was collected from a healthy female donor into 10 mL EDTA anti-coagulant tubes (Vacutainer #366643, Becton Dickinson, Franklin Lakes, N.J.) as described in Example 1. Immediately before experiments, the Vacutainer tubes were inverted several times by hand and 8.0 mL of blood were pipetted into a sterile test tube. Then 100 μL of the *E. cloacae* stock solution were added to the blood and mixed by lightly vortexing for 10 seconds.

Then 7.0 mL of the blood and bacteria mixture were pipetted into the hollow disk that had been cleaned as described in Example 1. Next 1.5 mL sterile PBS was pipetted as uniformly as possible into the pool of blood. Immediately the disk was accelerated for 22 seconds to 3000 rpm and held at that speed for 38 seconds. The disk was then decelerated from 3000 to 300 rpm over 65 seconds, and then decelerated linearly from 300 to 0 rpm over a time of 240 seconds. There was no remixing of the cell-pack and the plasma layer. When the disk came to rest, the plasma, which contained some bacteria, drained into the bowl of the disk. There was a small amount of streaking of red color into the amber-colored plasma. All of the plasma that flowed down was pipetted into a pre-weighed sterile test tube. The tube was weighed again to determine the weight of the plasma, which was converted to a volume of plasma assuming a density of 1.024 g/mL. In four replicates, the volumes of recovered plasma were 3.95, 4.11, 4.15 and 4.01 mL for an average of 4.06 mL.

The bacteria in the recovered plasma were collected by filtration and the colony forming units (CFUs) were quantified as described in Example 1. In these 4 replicates, the colony counts on the 4 filters were 609, 615, 623 and 601 CFUs.

Calibration of stock solution was done as described in Example 1. In these replicates, the stock solution contained 9,408 CFU/mL, the concentration in the blood was 117 CFU/mL, and the amount of CFUs pipetted into the hollow device was 823 CFU. In these 4 replicates, the percentage of bacteria in the recovered plasma and collected on the filter was 74, 75, 76 and 73%, producing an average of 74% recovery of CFUs from the bacteria-spiked blood sample.

Example 13. Stability of Plasma and Cell-Pack Layers During Deceleration

In this example, a series of experiments were done with male or female blood that was anticoagulated with EDTA, using the rotation and control system described in Example 8. Two types of transparent (VeroClear™ Resin) hollow rotating disks were used. One disk was the same disk as used in Example 1, and is called the "baffled disk". The other disk had the same weir design, and the same volume in the vestibule as the baffled disk, but did not contain any baffles; it is called the "non-baffled" disk. These experiments were designed to determine if the baffles affected the stability of the blood during deceleration. A Phantom v1610 camera (Vision Research, Wayne, N.J.) was mounted and focused on the edge of the disk, viewing downward through the transparent lid into the vestibule, and focusing on the interface between the clarified plasma layer and the cell-pack layer. The camera images were stored in a continuous memory loop such that the previous 18 seconds were always stored in the camera memory. A volume of 7.0 mL of blood without bacteria was added to the hollow disk. Then 1.5 mL of PBS was added to the blood in the disk. The disk was rotated up to 3000 rpm in 12 seconds, and held at 3000 rpm for 48 seconds. Then the disk was then decelerated at a constant deceleration rate of 100 rpm/s, 80 rpm/s, 50 rpm/s, 30 rpm/s, 20 rpm/s, 10 rpm/s, 5 rpm/s, 2 rpm/s or 1 rpm/s. During deceleration the images of the interface between plasma and cell-pack was recorded at 1000 frames per second. The operator watched the interface between plasma and cell-pack and stopped the camera immediately when remixing was observed. Then the operator reviewed the previous 18 seconds of captured images and identified the onset of instability of the interface. By knowing the time that the fluctuation appeared, and the deceleration rate, the operator calculated the rotational velocity (in rpm) at which the instability appeared. The data from these experiments are plotted in FIG. 9.

Results showed that when the deceleration rate is greater, the angular velocity at which instability occurs is greater. The data showed that within experimental scatter, there was no difference in stability between male and female blood. There was no difference in stability attributed to the presence or absence of baffles.

The observed points of instability form a band in FIG. 9. To the right of these points in the data set is a region of stable deceleration. To the left of the points is a region of instability. This data indicates how to design an optimal deceleration scheme for this 12-cm-diameter disk. Initially one could decelerate quickly at a high value of rpm/sec when the angular velocity is high; but as the rpm decreases, the rate of deceleration should also decrease to avoid crossing into the unstable region. The optimal deceleration scheme would be one that stays to the right of the data points, but close to the boundary of data points shown in FIG. 9.

LITERATURE REFERENCES

M. Amasia and M. Madou (2010) "Large-volume centrifugal microfluidic device for blood plasma separation," *Bioanalysis*, 2, 1701-10.

J. S. Beveridge, J. R. Stephens, and M. E. Williams (2011) "The Use of Magnetic Nanoparticles in Analytical Chemistry," *Annual Review of Analytical Chemistry*, 4, 4, 251-273.

Y. W. Chu, D. A. Engebretson, and J. R. Carey (2013) "Bioconjugated Magnetic Nanoparticles for the Detection of Bacteria," *Journal of Biomedical Nanotechnology*, 9, 1951-1961.

D. O. Cooney (1976) Biomedical Engineering Principles, vol. 2. New York: Marcel Dekker.

D. Di Carlo (2009) "Inertial microfluidics," *Lab on a Chip*, 9, 3038-3046.

D. J. Diekema and M. A. Pfaller (2013) "Rapid detection of antibiotic-resistant organism carriage for infection prevention," *Clinical Infectious Diseases*, 56, 1614-20.

M. Gao, Q. L. Hu, G. X. Feng, N. Tomczak, R. R. Liu, B. G. Xing, B. Z. Tang, and B. Liu (2015) "A Multifunctional Probe with Aggregation-Induced Emission Characteristics for Selective Fluorescence Imaging and Photodynamic Killing of Bacteria Over Mammalian Cells," *Advanced Healthcare Materials*, 4, 659-663.

S. Haeberle, T. Brenner, R. Zengerle, and J. Ducree (2006) "Centrifugal extraction of plasma from whole blood on a rotating disk," *Lab on a Chip*, 6, 776-81.

J. Hedman and P. Radstrom (2013) "Hou '12," in PCR Detection of Microbioal Pathogens, vol. 943, Methods in Molecular Biology, M. Wilkes, Ed.: Springer, pp. 17-48.

P. C. Hiemenz and R. Rajagopalan (1997) Principles of Colloid and Surface Chemistry, 3rd ed. New York: Marcel Dekker.

A. P. Hooper and W. G. C. Boyd (1983) "Shear-flow instability at the interface between two viscous fluids," *Journal of Fluid Mecanics.*, 128, 507-528.

H. W. Hou, H. Y. Gan, A. A. Bhagat, L. D. Li, C. T. Lim, and J. Han (2012) "A microfluidics approach towards high-throughput pathogen removal from blood using margination," *Biomicrofluidics*, 6, 24115-2411513, 1-13.

J. H. Kang, M. Super, C. W. Yung, R. M. Cooper, K. Domansky, A. R. Graveline, T. Mammoto, J. B. Berthet, H. Tobin, M. J. Cartwright, A. L. Watters, M. Rottman, A. Waterhouse, A. Mammoto, N. Gamini, M. J. Rodas, A. Kole, A. Jiang, T. M. Valentin, A. Diaz, K. Takahashi, and D. E. Ingber (2014) "An extracorporeal blood-cleansing device for sepsis therapy," *Nature Medicine*, 20, 1211-1216.

S. Kleinschmidt, F. Huygens, J. Faoagali, I. U. Rathnayake, and L. M. Hafner (2015) "*Staphylococcus epidermidis* as a cause of bacteremia," *Future Microbiology*, 10, 1859-1879.

A. Kumar, D. Roberts, K. E. Wood, B. Light, J. E. Parrillo, S. Sharma, R. Suppes, D. Feinstein, S. Zanotti, L. Taiberg, D. Gurka, A. Kumar, and M. Cheang (2006) "Duration of hypotension before initiation of effective antimicrobial therapy is the critical determinant of survival in human septic shock," *Critical Care Medicine*, 34, 1589-96.

J. J. Lee, K. J. Jeong, M. Hashimoto, A. H. Kwon, A. Rwei, S. A. Shankarappa, J. H. Tsui, and D. S. Kohane (2014) "Synthetic ligand-coated magnetic nanoparticles for microfluidic bacterial separation from blood," *Nano Letters*, 14, 1-5.

W. M. Leevy, J. R. Johnson, C. Lakshmi, J. Morris, M. Marquez, and B. D. Smith (2006) "Selective recognition of bacterial membranes by zinc(II)-coordination complexes," *Chemical Communications*, 1595-1597.

A. J. Mach and D. Di Carlo (2010) "Continuous scalable blood filtration device using inertial microfluidics," *Biotechnology & Bioengineering*, 107, 302-11.

I. Mattsby-Baltzer, T. Bergstrom, K. McCrea, R. Ward, L. Adolfsson, and O. Larm (2011) "Affinity apheresis for treatment of bacteremia caused by *Staphylococcus aureus* and/or methicillin-resistant *S. aureus* (MRSA)," *Journal of Microbiology & Biotechnology*, 21, 659-664.

O. Neth, D. L. Jack, A. W. Dodds, H. Holzel, N. J. Klein, and M. W. Turner (2000) "Mannose-binding lectin binds to a range of clinically relevant microorganisms and promotes complement deposition," *Infection and Immunity*, 68, 688-693.

G. Patel, S. Huprikar, S. H. Factor, S. G. Jenkins, and D. P. Calfee (2008) "Outcomes of carbapenem-resistant *Klebsiella pneumoniae* infection and the impact of antimicrobial and adjunctive therapies," *Infection Control & Hospital Epidemiology*, 29, 1099-106.

P. Pranay, R. G. Henriquez-Rivera, and M. D. Graham (2012) "Depletion layer formation in suspensions of elastic capsules in Newtonian and viscoelastic fluids," *Physics of Fluids*, 24, 61902, 1-30.

R. Skalak and S. Chien (1986) Handbook of Bioengineering. New York: McGraw Hill.

S. Q. Wang, F. Inci, T. L. Chaunzwa, A. Ramanujam, A. Vasudevan, S. Subramanian, A. C. F. Ip, B. Sridharan, U. A. Gurkan, and U. Demirci (2012) "Portable microfluidic chip for detection of *Escherichia coli* in produce and blood," *International Journal of Nanomedicine*, 7, 2591-2600.

Z. G. Wu, B. Willing, J. Bjerketorp, J. K. Jansson, and K. Hjort (2009) "Soft inertial microfluidics for high throughput separation of bacteria from human blood cells," *Lab on a Chip*, 9, 1193-1199.

P. Yagupsky and F. S. Nolte (1990) "Quantitative aspects of septicemia," *Clinical Microbiology Reviews*, 3, 269-79.

REFERENCES TO PATENTS

U.S. PATENTS

| | | |
|---|---|---|
| 9,470,618 B2 | Mar. 15, 2013 | Farrell et al. |
| 9,186,672 B2 | Apr. 18, 2011 | Amasia et al. |
| 9,150.631 B2 | Jan. 19, 2010 | Super et al. |
| 8,208,138 B2 | Sep. 24, 2009 | Papautsky et al. |
| 6,733,433 B1 | Dec. 24, 1998 | Fell |
| 5,554,293 A | Jun. 28. 1993 | Uhoch |
| 5,417,650 A | Mar. 2, 1992 | Gordon |
| 4,935,002 A | Jun. 29, 1988 | Gordon |

U.S. APPLICATIONS

| | | |
|---|---|---|
| US20140271490 A1 | Mar. 13, 2013 | Matosziuk et al. |
| US20140212335 A1 | Jan. 29, 2013 | Lee et al. |
| US20130306566 A1 | May 18, 2012 | Mao et al. |

What is claimed is:

1. A method for separating a particle from an original suspension of particles in a fluid, the fluid including red and white blood cells where the particle being separated is not a red or white blood cell, and has a sedimentation velocity that is slower than the sedimentation velocity of an average red blood cell, the method comprising:
   a. placing at least 0.5 ml of the original suspension within a cavity of a hollow device, the cavity having fluid communication with at least one partly open channel located along a side of the hollow device, the cavity of internal geometry such that when rotated a volume of the original suspension is forced into the least one partly open channel and forms a film along a back wall of the at least one partly open channel;
   b. rotating the hollow device for at least a time in which a combination of rotation time and angular velocity of the hollow device allows a plurality of layers to form by sedimentation within the film, including a first layer comprising a greater red blood cell number density than the number density of red blood cells in the original suspension and a second layer comprising a red blood cell number density less than the number density of red blood cells in the original suspension;
   c. slowing the spinning of the hollow device in a manner to prevent remixing of the first and second layers, the particle being separated located within the second layer; and
   d. stopping the spinning of the hollow device, providing gravity driven migration of the first layer into the at least one partly open channel, which forces at least a portion of the second layer into the cavity of the hollow device for collection.

2. The method of claim 1 in which at least one of the particles in the original suspension is selected from the group consisting of platelets, bacteria, microorganisms, viruses, proteins, polymer particles, organic particles, and inorganic particles.

3. The method of claim 1 in which the volume of the original suspension is between 0.5 ml and 1000 ml.

4. The method of claim 1 in which an average thickness of the film is between 0.2 mm and 10 mm.

5. The method of claim 1, in which the original suspension of particles in a fluid comprises blood to which was added at least one additional particle or at least one additional chemical selected from platelets, bacteria, microorganisms, viruses, proteins, particles of biological origin, polymer particles, organic particles, and inorganic particles anticoagulants, diluents, wetting agents, platelet aggregants, cell aggregants, platelet disrupters, and cell disrupters.

6. The method of claim 1 wherein the method further comprises concentrating the particles within the second layer by a process including one or more of filtration through a porous filter, ultrafiltration, centrifugation, size exclusion chromatography, physical capture in porous media, chemical capture in porous media, physical capture on magnetic beads, physical capture on non-magnetic beads, chemical capture on magnetic beads, chemical capture on non-magnetic beads, physical capture on bubbles, and chemical capture on bubbles.

7. A method for batchwise separation of at least one bacterium from red and white blood cells in a blood suspension, the method comprising:
   a. placing a volume of at least 0.5 mL of the blood suspension within a cavity of a hollow device, the cavity having fluid communication with at least one partly open channel located along a side of the hollow device, the cavity of internal geometry such that when rotated a portion of the blood suspension is forced into the at least one partly open channel and forms a film along a back wall of the at least one partly open channel;
   b. rotating the hollow device for at least a time in which a combination of rotation time and angular velocity of the hollow device allows a cell-pack layer and a partly clarified layer to form within the film, the cell-pack layer having a thickness one-tenth or greater the thickness of the film;
   c. slowing the spinning of the hollow device in a manner to prevent remixing of the partly clarified layer with the cell-pack layer, the bacterium being separated located within the partly clarified layer; and
   d. stopping the spinning of the hollow device, providing gravity driven migration of the cell-pack layer into the at least one partly open channel, which forces at least a portion of the partly clarified layer into the cavity of the hollow device for collection.

8. The method of claim 7 in which the volume of the blood suspension is between 0.5 ml and 1000 ml.

9. The method of claim 7 in which an average thickness of the film is between 0.2 mm and 10 mm.

10. The method of claim 7, the method further comprising adding a chemical to the blood suspension selected from one or more anticoagulants, diluents, wetting agents, platelet aggregants, cell aggregants, platelet disrupters, and cell disrupters.

11. The method of claim 7, the method further comprising adding a chemical to the hollow device, the chemical selected from one or more anticoagulants, diluents, wetting agents, platelet aggregants, cell aggregants, platelet disrupters, and cell disrupters.

12. The method of claim 7 wherein the method further comprises concentrating the bacteria within the separated partly clarified layer by a process including one or more of filtration through a porous filter, ultrafiltration, centrifugation, size exclusion chromatography, physical capture in porous media, chemical capture in porous media, physical capture on magnetic beads, physical capture on non-magnetic beads, chemical capture on magnetic beads, chemical capture on non-magnetic beads, physical capture on bubbles, and chemical capture on bubbles.

13. The method of claim 7 in which bacterial concentration in the blood suspension is between 1 and 10,000 colony forming units per milliliter.

* * * * *